United States Patent [19]

Sugihara et al.

[11] Patent Number: 4,997,836

[45] Date of Patent: Mar. 5, 1991

[54] TRISUBSTITUTED PIPERAZINE COMPOUNDS, THEIR PRODUCTION AND USE

[75] Inventors: Hirosada Sugihara, Osaka; Kohei Nishikawa, Kyoto, both of Japan

[73] Assignee: Takeda Chemical Industries, Ltd., Osaka, Japan

[21] Appl. No.: 433,990

[22] Filed: Nov. 9, 1989

[30] Foreign Application Priority Data

Nov. 11, 1988 [JP] Japan .................................. 63-286427
Oct. 5, 1989 [JP] Japan ................................... 1-261131

[51] Int. Cl.⁵ .................. A61K 31/495; C07D 401/12; C07D 403/12; C07D 407/12
[52] U.S. Cl. .................................... 514/253; 514/252; 514/255; 544/359; 544/360; 544/361; 544/362; 544/363; 544/364; 544/365; 544/366; 544/367; 544/368; 544/369; 544/370; 544/372; 544/373; 544/374; 544/375; 544/376; 544/377; 544/378; 544/379; 544/380; 544/382; 544/383; 544/384; 544/386; 544/387; 544/388; 544/389; 544/390; 544/391
[58] Field of Search ....................... 514/252, 253, 255; 544/362, 364, 359, 360, 361, 363, 365, 366, 367, 368-370, 372-380, 382-384, 386-391

[56] References Cited

U.S. PATENT DOCUMENTS

| 4,243,665 | 1/1981 | Purcell et al. | 544/391 |
| 4,263,299 | 4/1981 | Buckle et al. | 544/376 |
| 4,374,990 | 2/1983 | Weber et al. | 544/376 |
| 4,383,995 | 5/1983 | Delbarre et al. | 544/376 |
| 4,556,656 | 12/1985 | McCall | 544/376 |
| 4,826,975 | 5/1989 | Picciola et al. | 544/391 |
| 4,845,094 | 7/1989 | Tatsuoka et al. | 544/376 |
| 4,870,175 | 9/1989 | Suzuki et al. | 544/391 |

FOREIGN PATENT DOCUMENTS

| 0284359 | 9/1988 | European Pat. Off. . |
| 0318235 | 5/1989 | European Pat. Off. . |
| 1187706 | 4/1970 | United Kingdom ................ 544/376 |

OTHER PUBLICATIONS

Abstract of WO79/00426.
Sugihara et al, Chem. Abst. 111-225318v (1989).
Sugihara et al, Chem. Abst. 110-95274u (1989).
Chemical Patents Index Basic Abstracts Journal Section B, 86-179263/28, Japanese Unexamined Patent Publication No. 112060/1986.
Chemical Patents Index Basic Abstracts Journal Section B, 87-016682/03, Japanese Unexamined Patent Publication No. 233675/1986.

Primary Examiner—Cecilia Shen
Attorney, Agent, or Firm—Wegner, Cantor, Mueller & Player

[57] ABSTRACT

Novel trisubstituted piperazine compounds of the formula (I) and pharmaceutically acceptable salts thereof:

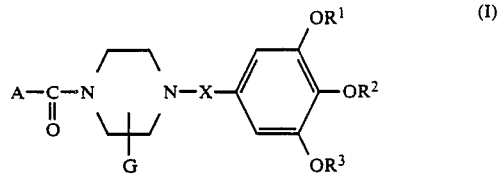

wherein $R^1$, $R^2$ and $R^3$ are lower alkyl groups; A is a phenyl group, a hydrocarbon group formed by condensation of two or three 5- to 8-membered rings, a monocyclic 5- to 8-membered heterocyclic group containing 1 to 3 hetero-atoms selected from the class consisting of nitrogen, oxygen and sulfur, a dicyclic heterocyclic group formed by condensation of a benzene ring with a 5- to 8-membered hetero-ring containing 1 to 3 hetero-atoms selected from the class consisting of nitrogen, oxygen and sulfur, a tricyclic heterocyclic group formed by condensation of (i) a 5- to 8-membered hetero-ring containing 1 to 3 hetero-atoms selected from the class consisting of nitrogen, oxygen and sulfur, and (ii) a benzene ring, and (iii) a benzene ring or a 5- to 8-membered hetero-ring containing 1 to 3 hetero-atoms selected from the class consisting of nitrogen, oxygen and sulfur, or a styryl group of the formula: Ar—$CR^4$=$CR^5$— wherein Ar is a phenyl group, and $R^4$ and $R^5$ are independently hydrogen or a lower alkyl group, the phenyl group represented by A or Ar, the hydrocarbon group represented by A, the monocyclic 5- to 8-membered heterocyclic group represented by A, the dicyclic heterocyclic group represented by A and the tricyclic heterocyclic group represented by A being unsubstituted or substituted by one or more substituents selected from the class consisting of a lower alkyl group, a halo lower alkyl group, a hydroxy lower alkyl group, an acyloxy lower alkyl group, a lower alkoxy lower alkyl group, a lower alkoxy group, a halo lower alkoxy group, a lower alkoxycarbonyl lower alkoxy group, a lower alkenyloxy group, aralkyloxy group, a lower alkoxy lower alkoxy group, a lower alkoxycarbonyl group, carboxyl group, carbamoyl group, an N,N-di-lower alkylcarbamoyl group, an N-lower alkylcarbamoyl group, halo group, cyano group, nitro group, hydroxy group, acyloxy group, amino group, a lower alkylsulfonylamino group, acylamino group, a lower alkoxycarbonylamino group, acyl group, mercapto group, a lower alkylthio group, a lower alkylsulfinyl group, a lower alkylsulfonyl group and oxo group; X is methylene group, carbonyl group or thiocarbonyl group and G is a group of the formula: —$CH_2$—$_n$-Z—$R^6$ wherein n is an integer of 0 to 2, Z is a chemical bond, O, S, SO, $SO_2$, CO, COO, OCO, $OCONR^7$, $CONR^7$ or $NR^7$ (wherein $R^7$ is hydrogen, a lower alkyl group, a lower haloalkyl group, a lower alkenyl group or a lower alkoxycarbonyl group), and $R^6$ is hydrogen, a lower alkyl group, a lower haloalkyl group or a lower alkenyl group, provided that, when n is O and Z is chemical bond, $R^6$ is not hydrogen or a lower alkyl group are useful as a platelet activating factor antagonist.

32 Claims, No Drawings

TRISUBSTITUTED PIPERAZINE COMPOUNDS, THEIR PRODUCTION AND USE

BACKGROUND OF THE INVENTION

This invention relates to trisubstituted piperazine compounds useful as medicines. More specifically, the present invention relates to compounds represented by the formula:

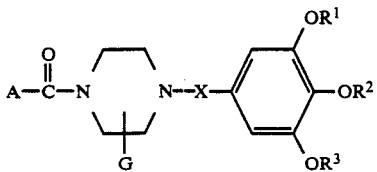

wherein $R^1$, $R^2$, and $R^3$ represent a lower alkyl group, A stands for an optionally substituted phenyl group, an optionally substituted condensed polycyclic hydrocarbon group, an optionally substituted hetero-cyclic group or a styryl group represented by the formula $Ar-CR^4=CR^5-$ wherein Ar stands for an optionally substituted phenyl group, and $R^4$ and $R^5$ respectively stand for hydrogen or a lower alkyl group, X stands for a methylene group, carbonyl group or thiocarbonyl group, and G stands for a group represented by the formula: $-(CH_2)_n-Z-R^6$ wherein n denotes an integer of 0 to 2, Z stands for a chemical bond, O, S, SO, $SO_2$, CO, COO, OCO, OCONR$^7$, CONR$^7$ or NR$^7$ (wherein $R^7$ stands for hydrogen, a lower alkyl group, a lower haloalkyl group, a lower alkenyl group or a lower alkoxycarbonyl group), and $R^6$ stands for hydrogen, a lower alkyl group, a lower haloalkyl group, a lower alkenyl group, a lower alkynyl group or a lower cycloalkyl group, provided that, when n=O and Z=chemical bond, $R^6$ is not hydrogen or a lower alkyl group and pharmaceutically acceptable salts thereof. The compounds are useful as platelet activating factor (PAF) antagonists.

PAF has a phospholipid structure and is a chemical transmitter existing in a living body. It has been made clear that PAF is closely concerned with allergy, anaphylaxis, inflammation, etc. and it has also been known that PAF has a strong hypotensive activity and platelet agglutinating activity. On administering PAF to an animal, the animal may in some cases be killed from shock. Symptoms caused by the shock from PAF have much resemblance to those caused by the shock from endotoxin, and it has been considered that PAF is concerned with the endotoxin shock.

On the other hand, while a variety of compounds having PAF-antagonistic activity have been known, very few of them are satisfactory in PAF-antagonistic activity in a living body. And, even when the PAF-antagonistic activity in a living body is satisfactory, not a few of those compounds have some restrictions in the administration method.

DETAILED DESCRIPTION

The present invention is to provide the compounds represented by the above-mentioned formula (I) and pharmaceutically acceptable salts thereof.

Referring to the formula (I), examples of the condensed polycyclic hydrocarbon groups shown by A include bicyclic or tricyclic hydrocarbon groups which may optionally be saturated partially, more specifically, hydrocarbon groups formed by condensation of two or three 5- to 8-membered rings, such as pentalenyl, indenyl (1H-indenyl, 2H-indenyl), indanyl, naphthyl, dihydronaphthyl (1,2-dihydronaphthyl, 2,3-dihydronaphthyl), tetrahydronaphthyl (1,2,3,4-tetrahydronaphthyl, etc.), hexahydronaphthyl (1,2,3,4,5,6-hexahydronaphthyl, etc.), azulenyl, heptalenyl, biphenylenyl, indacenyl (as-indacenyl, s-indacenyl), acenaphthylenyl, acenaphthenyl, phenalenyl, phenanthryl, dihydrophenanthryl (1,2-dihydrophenanthryl), tetrahydrophenanthryl (1,2,3,4-tetrahydrophenanthryl, etc.), hexahydrophenanthryl, anthryl, dihydroanthryl (9,10-dihydroanthryl, etc.), tetrahydroanthryl, hexahydroanthryl, octahydroanthryl, fluorenyl (3H-fluorenyl, 9H-fluorenyl, etc.), dihydrofluorenyl, tetrahydrofluorenyl, benzocycloheptenyl (5H-benzocyclo-heptenyl, etc.), dihydrobenzocycloheptenyl (6,7-dihydro-5H-benzocycloheptenyl, etc.), tetrahydrobenzocycloheptenyl (6,7,8,9-tetrahydro-5H-benzocycloheptenyl, etc.), dibenzocycloheptenyl (5H-dibenzo[a,b]cycloheptenyl, 5H-dibenzo [a,c]cycloheptenyl, etc.), naphthocycloheptenyl (6H-naptho[b]cycloheptenyl, etc.), dihydronaphthocycloheptenyl (7,8-dihydro-6H-naphtho[b]cycloheptenyl, etc.), benzocyclooctenyl, dihydrobenzocyclooctenyl (5,6-dihydrobenzocyclooctenyl, etc.), tetrahydrobenzocyclooctenyl (5,6,7,8-tetrahydrobenzocyclooctenyl, etc.), hexahydrobenzocyclooctenyl, octahydrobenzocyclooctenyl, etc.

Referring to the formula (I), examples of the heterocyclic groups shown by A include monocyclic, dicyclic and tricyclic heterocyclic groups which may optionally be saturated partially. Examples of the monocyclic heterocyclic groups include, among others, 5- to 8-membered heterocyclic groups containing 1 to 3 hetero atoms selected from nitrogen, oxygen and sulfur, such as pyridyl (2-pyridyl, 3-pyridyl, 4-pyridyl), thienyl (2-thienyl, 3-thienyl), furyl, thiazolyl (2thiazolyl, 2-phenyl-4-thiazolyl, 2-pyridyl-4-thiazolyl, etc.), etc.

Examples of the dicyclic heterocyclic groups which may optionally be saturated partially include, among others, condensed dicyclic heterocyclic groups formed by condensation of benzene ring with a 5- to 8-membered heteroring containing 1 to 3 hetero atoms selected from nitrogen, oxygen and sulfur, such as quinolyl (2-quinolyl, 3-quinolyl, 4-quinolyl, 5-quinolyl, 6-quinolyl, 7-quinolyl), isoquinolyl (3-isoquinolyl, etc.), indolyl (5-indolyl, etc.), benzothiazolyl (2-benzothiazolyl, etc.), 1,3-benzodioxolyl (1,3-benzodioxol-5-yl, etc.), benzofuranyl (2-benzofuranyl, etc.), 2,3-dihydrobenzofuranyl, benzopyranyl (2-benzopyranyl, 3-benzopyranyl, etc.), 3,4dihydrobenzopyranyl, 1-benzoxepinyl (1-benzoxepin-4-yl,1-benzoxepin-8-yl, etc.), 2,3-dihydro-1-benzoxepinyl (2,3-dihydro-1-benzoxepin-4-yl, etc.), 2,3,4,5-tetrahydro-1-benzoxepinyl, 1-benzothiepinyl, 2,3-dihydro-1-benzothiepinyl (2,3-dihydro-1-benzothiepin-4-yl, etc.), 2,3,4,5-tetrahydro-1-benzothiepinyl, 3,4-dihydro-2H-1,5-benzoxepinyl, 2,3-dihydro-1,4benzoxynyl[1,4-benzoxanyl] (2,3-dihydro-1,4-benzodioxin-6-yl, etc.), chromenyl (2H-chromen-3-yl, etc.), chromanyl (3-chromanyl, etc.), imidazo[1,2-a]pyridyl, etc.

And, examples of the tricyclic heterocyclic groups which may optionally be saturated partially include, among others, a condensed tricyclic heterocyclic group formed by condensation of (i) a 5- to 8-membered hetero-ring containing 1 to 3 heteroatoms selected from nitrogen, oxygen and sulfur, (ii) benzene ring and (iii) benzene ring or 5- to 8-membered hetero-ring containing 1 to 3 hetero-atoms selected from nitrogen, oxygen and sulfur, more specifically, dibenzofuranyl (2-dibenzofuranyl, etc.), 3,4-dihydrobenzofuranyl (3,4-dihydrodibenzofuran-2-yl, etc.), 1,2,3,4tetrahydrodibenzofuranyl, dibenzothiophenyl (2dibenzothiophenyl, etc)), 3,4-dihydrodibenzothiophenyl (3,4-dihydrobenzothiophen-2-yl, etc.), 1,2,3,4tetrahydrodibenzothiophenyl (1,2,3,4-tetrahydrobenzothiophen-2-yl, etc.), naphtho[2,3-d]-1,3-dioxolyl, 5,6-dihydronaphtho[2,3-d]-1,3-dioxolyl (5,6-dihydronaphtho[2,3-d]-1,3-dioxol-7-yl, etc.), 5,6,7,8-tetrahydronaphtho[2,3-d]-1,3-dioxolyl, naphtho[2,3-b]-1,4-dioxanyl, 6,7-dihydronaptho[2,3-b]-1,4-dioxanyl (6,7-dihydronaphtho[2,3-b]-1,4-dioxan-8-yl, etc.), 5H-cyclohepta[f]-1,3-benzodioxolyl, 6,7-dihydro-5H-cyclohepta[f]-1,3-benzodioxolyl (6,7-dihydro-5H-cyclohepta[f]-1,3-benzodioxol-8-yl, etc.), 6H-cyclohepta[g]-1,4-benzodioxanyl, 7,8-dihydro-6H-cyclohepta[g]-1,4-benzodioxanyl (7,8-dihydro-6H-cyclo 1,4-benzodioxan-9-yl, etc.), dibenzo-pdioxynyl, xanthenyl, 1,2-dihydroxanthenyl, naphtho[2,1b]furanyl, 1,2,8,9-tetrahydronaphtho[2,1-b]furanyl, 2,3,5,6-tetrahydronaphtho[2,1-b]furanyl, etc.

Referring to the formula (I), examples of the lower alkyl groups shown by $R^4$ or $R^5$ in the styryl group of the formula Ar—$CR^4$=$CR^5$— shown by A include alkyl groups whose carbon number ranges from about 1 to about 4, such as methyl, ethyl, propyl, isopropyl, butyl, isobutyl, secbutyl, tert-butyl, etc.

The phenyl group, condensed polycyclic hydrocarbon groups, heterocyclic groups or the phenyl group moiety of the styryl group shown by the above-mentioned A or Ar may have one or more (preferably not more than 4) substituents such as, among others, a lower alkyl group, a halo lower alkyl group, a hydroxy lower alkyl group, a acyloxy lower alkyl group, a lower alkoxy lower alkyl group, a lower alkoxy group, a halo lower alkoxy group, a lower alkoxy carbonyl lower alkoxy group, a lower alkenyloxy group, aralkyloxy group, a lower alkoxy lower alkoxy group, a lower alkoxycarbonyl group, carboxyl group, carbamoyl group, an N,N-di-lower alkylcarbamoyl group, an N-lower alkylcarbamoyl group, halo group, cyano group, nitro group, hydroxy group, acyloxy group, amino group, a lower alkylsulfonylamino group, acylamino group, a lower alkoxycarbonylamino group, acyl group, mercapto group, a lower alkylthio group, a lower alkylsulfinyl group, lower alkylsulfonyl group and oxo group, and when the number of these substituents is two or more, the kinds of those substituents may be the same or different.

Lower alkyl groups as the above-mentioned substituents are exemplified by alkyl groups whose carbon number ranges from about 1 to about 4, such as methyl, ethyl, propyl, isopropyl, butyl, isobutyl, secbutyl, tert-butyl, etc. As the halo lower alkyl group, mention is made of alkyl groups whose carbon number ranges from about 1 to about 4, which are substituted with 1 to 3 halo groups, such as trifluoromethyl, fluoromethyl, chloromethyl, chloroethyl, fluoroethyl, etc. As the hydroxy lower alkyl group, mention is made of hydroxy alkyl groups whose carbon number ranges from about 1 to about 4, such as hydroxy-methyl, hydroxyethyl, hydroxypropyl, hydroxybutyl, etc. As the acyloxy lower alkyl group, mention is made of alkyl groups whose carbon number ranges from about 1 to about 4, which are substituted with, for example, a lower alkanoyloxy group whose carbon number ranges from about to about 5 or benzoyloxy group, such as acetoxyethyl, benzoyloxyethyl, etc. As the lower alkoxy lower alkyl group, mention is made of alkyl groups whose carbon number ranges from about 1 to about 4, which are substituted with, for example, an alkoxy group whose carbon number ranges from about 1 to about 4 such as methoxyethyl, ethoxyethyl, propoxyethyl, butoxyethyl, methoxypropyl, methoxybutyl, ethoxybutyl, etc. As the lower alkoxy group, mention is made of alkoxy groups whose carbon number ranges from about 1 to about 4 such as methoxy, ethoxy, propoxy, isopropoxy, butoxy, isobutoxy, sec-butoxy, tert-butoxy, etc. As the halo lower alkoxy group, mention is made of alkoxy groups whose carbon number ranges from about 1 to about 4, which are substituted with 1 to 3 halo groups such as chloroethoxy, fluoroethoxy, difluoroethoxy, trifluoroethoxy, chloropropoxy, chlorobutoxy, etc. As the lower alkoxy carbonyl lower alkoxy group, mention is made of alkoxy groups whose carbon number ranges from about 1 to about 4, which are substituted with an alkoxycarbonyl group, the carbon number of the alkoxy moiety of which ranges from about 1 to about 4, such as methoxycarbonylmethoxy, ethoxycarbonylmethoxy, butoxycarbonylmethoxy, methoxycarbonylpropoxy, ethoxycarbonylethoxy, etc. Examples of the lower alkenyloxy group include alkenyloxy groups whose carbon number ranges from 2 to about 5, such as vinyloxy, allyloxy, butenyloxy, etc. As the aralkyloxy group, mention is made of phenyl lower alkyloxy groups, the carbon number of the lower alkyl moiety of which ranges from about 1 to about 4, such as benzyloxy, phenethyloxy, 3-phenylproyloxy, α-methylphenethyloxy, α-methylbenzyloxy, α-ethylbenzyloxy, β-ethylphenethyloxy, β-methylphenethyloxy, etc. As the lower alkoxy lower alkoxy group, mention is made of alkoxy groups whose carbon number ranges from about 1 to about 4, which are substituted with, for example, an alkoxy group whose carbon number ranges from about 1 to about 4, such as ethoxymethoxy, methoxyethoxy, butoxyethoxy, ethoxypropoxy, etc. Examples of the lower alkoxycarbonyl group include alkoxycarbonyl groups, the carbon number of the alkoxy moiety of which ranges from about 1 to about 4, such as methoxycarbonyl, ethoxycarbonyl, propoxycarbonyl, butoxycarbonyl, etc. As the N,N-di-lower alkylcarbonyl groups, mention is made of N,N-dialkylcarbamoyl groups, the carbon number of each alkyl moiety of which ranges from about 1 to about 4, such as N,N-dimethylcarbamoyl, N,N-diethyl-carbamoyl, N,N-dipropylcarbamoyl, N,N-dibutylcarbamoyl, N-ethyl-N-methylcarbamoyl, etc., and groups forming 5- or 6-membered ring structure (e.g. N-pyrrolidinylcarbonyl, piperidinocarbonyl) by combining dialkyl moieties together As the N-lower alkylcarbamoyl group, mention is made of N-alkylcarbamoyl groups, the carbon number of the alkyl moiety of which ranges from about 1 to about 4, such as N-methylcarbamoyl, N-ethylcarbamoyl, N-propylcarbamoyl, N-butylcarbamoyl, etc. As the halo group, mention is made of halogeno groups such as chloro, fluoro, bromo, iodo, etc. As the acyloxy group, mention is made of alkanoyloxy groups, the carbon number of which ranges from about 2 to about 5, such as acetoxy, propanoyloxy, butyryloxy, pivaloyloxy, etc., and benzoyloxy group. As the lower alkylsulfonylamino group, mention is made of alkylsulfonylamino groups, the carbon number of which ranges from about 1 to about 4, such as methanesulfonylamino, ethanesulfonylamino, etc. Examples of the acylamino group include alkanoylamino groups, whose carbon number ranges from about 2 to about 5, such as acetamido, propanoylamino, butyrylamino, pivaloylamino, etc. and benzamido group. As the lower alkoxycarbonylamino group, mention is made of alkoxycarbonylamino groups, the carbon number of the alkoxy moiety of which ranges from about 1 to about 4, such as methoxycarbonylamino, ethoxycarbonylamino, propoxycarbonylamino, butoxycarbonylamino, etc. As the acyl group, mention is made of alkanoyl groups, the carbon number of which ranges from about 2 to about 5, such as acetyl, propanoyl, butyryl, pivaloyl, etc. and benzoyl group. As the lower alkylthio group, mention is made of alkylthio groups, the carbon number of which ranges from about 1 to about 4, such as methylthio, ethylthio, propylthio, butylthio, etc. As the lower alkylsulfinyl group, mention is made of alkylsulfinyl groups, the carbon number of which ranges from about 1 to about 4, such as methylsulfinyl, ethylsulfinyl, propylsulfinyl, butylsulfinyl, etc. As the lower alkylsulfonyl group, mention is made of alkylsulfonyl groups, the carbon number of which ranges from about 1 to about 4, such as methylsulfonyl, ethylsulfonyl, propylsulfonyl, butylsulfonyl, etc.

Specific examples of the optionally substituted phenyl group shown by the above-mentioned A include 3,4-dimethoxyphenyl, 3,4,5-trimethoxyphenyl, 3,4,5-triethoxyphenyl, 3-methoxy-5-nitro-4-n-propoxyphenyl, 3,4-dimethoxy-5-methylsulfonylphenyl, 3-chloro-4,5-dimethoxyphenyl, etc.

Specific examples of the optionally substituted condensed polycyclic hydrocarbon group shown by the above-mentioned A include 1-naphthyl, 2-naphthyl, 1-methoxy-2-naphthyl, 3-methoxy-2-naphthyl 6-methoxy-2naphthyl, 6,7-dimethoxy-2-naphthyl, 5,6,7-trimethoxy-2naphthyl, 6-butoxy-2-naphthyl, 6,7-dibutoxy-2-naphthyl, 7-methoxy-1,2-dihydro-3-naphthyl, 6,7-dimethoxy-1,2-dihydro-3-naphthvl-, 7,8-dimethoxy-1,2-dihydro-4-naphthyl, 6,7,8-trimethoxy-1,2-dihydro-3-naphthyl, 6,7- diethoxy-1,2-dihydro-3-naphthyl, 6,7-dipropoxy-1,2-dihydro-3-naphthyl, 6,7-dibutoxy-1,2-dihydro-3-naphthyl, 7-benzyloxy-1,2-dihydro-3-naphthyl 7-hydroxy-1,2-dihydro-3-naphthyl, 6,7-dibenzyloxy-1,2-dihydro-3-naphthyl, 6,7-dihydroxy-1 2-dihydro-3naphthyl, 6-methoxy-1,2,3,4-tetrahydro-2-naphthyl 7-acetoxy-1,2-dihydro-3-naphthyl, 6,7-diacetoxy-1 2-dihydro-3-naphthyl, 7-benzoyloxy-1,2-dihyd6,7-dibenzoyloxy-1,2-dihydro-3-naphthyl, 7-methoxy-8-nitro-1,2-dihydro-nitro-1,2-dihydro-3-naphthyl, 6,7-dimethoxy-8-nitro-1,2-dihydro-3-naphthyl, 7-ethoxycarbonylmethoxy-1 2-dihydro-3-naphthyl, 7-(2-methoxyethoxy)-1,2-dihydro-3-naphthyl 6 8-dimethyl-1,2-dihydro-3-naphthyl 6-hydroxymethyl-7-methoxy-1,2-dihydro-3-naphthyl, 6,8-dimethyl-7-nitro-1,2-dihydro-3-naphthyl, 7-(2-hydroxyethoxy)-1,2-dihydro-3-naphthyl, 7-(2,3-dimethoxypropoxy]-1,2-dihydro-3-naphthyl, 7-(3-methoxypropoxy)-1,2-dihydro-3naphthyl 6,7-bis(2-methoxyethoxy)-1,2-dihydro-3naphthyl, 5,6-dimethoxy-2-indanyl, 5,6-dimethoxy-1H-2indenyl, 3,4-dimethoxy-6,7-dihydro-5H-8benzocycloheptenyl, 2,3-dimethoxy-6,7-dihydro-5H-8benzocycloheptenyl, 2,3-diethoxy-6,7-dihydro-5H-8benzocycloheptenyl, 2,3-dipropoxy-6,7-dihydro-5H-8benzocycloheptenyl, 2,3-dibutoxy-6,7-dihydro-5H-8benzocycloheptenyl, 2-benzyloxy-3-methoxy-6,7-dihydro-5H-8-benzocycloheptenyl, 2-ethoxy-3-methoxy-6,7-dihydro-5H-8-benzocycloheptenyl, 2-propoxy-3-methoxy6,7-dihydro-5H-8-benzocycloheptenyl, 2-butoxy-3-methoxy-6,7-dihydro-5H-8-benzocycloheptenyl, 3-methoxy6,7-dihydro-5H-8-benzocycloheptenyl, 3-ethoxy-6,7-dihydro-5H-8-benzocycloheptenyl, 3-propoxy-6,7-dihydro5H-8-benzocycloheptenyl, 3-butoxy-6,7-dihydro-5H-8benzocycloheptenyl, 2,3-dimethyl-6,7-dihydro-5H-8benzocycloheptenyl, 3-benzyloxy-6,7-dihydro-5H-8-benzocycloheptenyl, 6,7-dihydro-5H-8-benzocycloheptenyl, 1,2,3-trimethoxy-6,7-dihydro-5H-8-benzocycloheptenyl, 7-ethoxy-1,2-dihydro-3-naphthyl, 7-propoxy-1,2-dihydro3-naphthyl, 7-butoxy-1,2-dihydro-3-dimethoxy-5,6,7,8-tetrahydro-9-benzocyclooctenyl, 5,6,7,8-tetrahydro-9-benzocyclooctenyl, 2,3-dihydro-3naphthyl, 1-indanyl, 2-indanyl, 1H-2-indenyl, 2,3-dimethoxy-6,7,8,9-tetrahydro-5H-6-benzocycloheptenyl, 6,7-dimethoxy-1-hydroxy-2-naphthyl, 6-mercapto-2naphthyl, 6-methylthio-2-naphthyl, 6-methanesulfonyl-2naphthyl, 1-oxo-1,2,3,4-tetrahydro-6-naphthyl, 1-oxo-1,2,3,4-tetrahydro-7-naphthyl, 1-oxo-5-indanyl, 1-oxo-6-indanyl, 1-hydroxy-1,2,3,4-tetrahydro-6-naphthyl, 1-hydroxy-1,2,3,4-tetrahydro-7-naphthyl, 1-hydroxy-5indanyl, 1-hydroxy-6-indanyl, 9-oxo-2-fluorenyl, 9-hydroxy-2-fluorenyl, 2-anthraquinonyl, etc.

Examples of the optionally substituted monocyclic, dicyclic or tricyclic heterocyclic groups shown by the above-mentioned A include 3-coumarinyl, 6-methoxy-3coumarinyl, 7-methoxy-3-coumarinyl, 6-methyl-3coumarinyl, 7-n-butoxy-3-coumarinyl, 6-methoxy-2benzofuranyl, 7-ethoxy-2-benzofuranyl, 1-hydroxy1,2,3,4-tetrahyirodibenzothiophen-2-yl, 3oxospiro[benzofuran-2(3H),1'-cyclopropan]-5-yl, 3-hydroxyspiro[benzofuran-2(3H),1'-cyclopropan]-5-yl, 7,8-dimethoxy-2,3-dihydro-1-benzoxepin-4-yl, 7-methoxy2,3-dihydro-1-benzoxepin-4-yl, 8-propoxy-2,3-dihydro-1-benzoxepin-4-yl, 7-methoxy-8-methyl-2,3-dihydro-1-benzoxepin-4-yl, 7,8-dimethoxy-2,3,4,5-tetrahydro-1-benzoxepin-4-yl, 7-chloro-8-methoxy-2,3-dihydro-1-benzoxepin-4-yl, 7,8-dimethyl-2,3-dihydro-1-benzoxepin4-yl, 7,8-dimethoxy-2,3-dihydro-1-benzothiepin-4-yl, 8methoxy-2,3-dihydro-1-benzothiepin-4-yl, 1-oxo-2,3-dihydro-1-benzothiepin-4-yl, 1,1-dioxo-2,3-dihydro-1-benzothiepin-4-yl, 7,8-dimethoxy-1-oxo-2,3-dihydro-1-benzothiepin-4-yl-, 7,8-dimethoxy-1,1-dioxo-2,3-dihydro1-benzothiepin-4-yl, 2-(3-pyridyl)-4-thiazolyl, 2-(3,4-dimethoxyphen-vl)-4-thiazoly1,2-(3-pyridyl)-4-thiazolyl, 2-(3,4-dimethoxyphenyl)-4-thiazolyl, etc.

Specific examples of the optionally substituted styryl group ($Ar-CR^4=CR^5-$ : wherein each symbol is of the same meaning as defined above) include p-methoxystyryl, p-methoxy-α-methylstyryl, 3,4-dimethoxy-α-methylstyryl, p-methoxy-α-ethylstyryl, 3,4-dimethoxyα-ethylstyryl, p-propoxy-α-methylstyryl, 3,4-dimethoxy-β-methylstyryl, etc.

Preferable examples of an optionally substituted phenyl group represented by the above-mentioned A or Ar include phenyl group substituted with 1 to 3 lower alkoxy groups (more preferably methoxy or ethoxy).

Preferable examples of the optionally substituted heterocyclic groups shown by the above-mentioned A include optionally substituted oxygen-containing condensed di- or tri-cyclic heterocyclic groups (benzo-1,3-dioxolyl, coumarinyl, 2,3-dihydro-1-benzoxepinyl, dibenzofuranyl, 5,6-dihydronaphtho[2,3-d]-1,3-dioxolyl, 6,7-dihydrocyclohepta[f]-1,3-benzodioxolyl, etc.). Further preferable groups are heterocyclic groups represented by the formula:

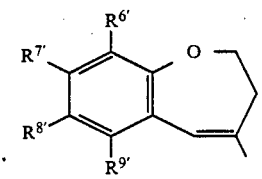 (I')

wherein $R^{6'}$, $R^{7'}$, $R^{9'}$ each stand for hydrogen, a lower alkyl group, a halo lower alkyl group, a hydroxy lower alkyl group, an acyloxy lower alkyl group, a lower halo lower alkyl group, a lower alkoxy group, a halo lower alkoxy group, a lower alkoxycarbonyl lower alkoxy group, a lower alkenyloxy group, aralkyloxy group, a lower alkoxy lower alkoxy group, a lower alkoxycarbonyl group, carboxyl group, carbamoyl group, an N,N-di-lower alkylcarbamoyl group, an N-lower alkylcarbamoyl group, halo group, cyano group, nitro group, hydroxyl group, acyloxy group, amino group a lower alkylsulfonylamino group, acyl amino group, a lower alkoxycarbonylamino group, acyl group, mercapto group, a lower alkylthio group, a lower alkylsulfinyl group or a lower alkylsulfonyl group (more preferably hydrogen, a lower alkoxy group or a lower alkyl group)], and, among them, especially preferable ones are the heterocyclic groups of the above mentioned formula wherein $R^{6'}$ and $R^{9'}$ stand for hydrogen, and, $R^{7'}$ and $R^{8'}$ respectively stand for a lower alkoxy group (more preferably methoxy or ethoxy).

Preferable examples of the optionally substituted condensed polycyclic hydrocarbon groups shown by the above-mentioned A include those represented by the formula:

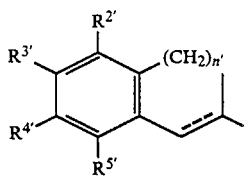

wherein the broken line designates possible presence of a double bond (preferably the presence of a double bond); n' denotes an integer of 1 to 4 (preferably 2 or 3); and $R^{2'}$, $R^{3'}$, and $R^{5'}$ respectively stand for hydrogen, a lower alkyl group, a halo lower alkyl group, a hydroxy lower alkyl group, an acyloxy lower alkyl group, a lower alkoxy lower alkyl group, a lower alkoxy group, an N-lower alkylcarbamoyl group, a halo lower alkoxy group, a lower alkoxycarbonyl lower alkoxy group, a lower alkenyloxy group, aralkyloxy group, a lower alkoxy lower alkoxy group, a lower alkoxy lower alkyl group, a lower alkoxycarbonyl group, carboxyl group, carbamoyl group, an N,N-di-lower alkylcarbamoyl group, halo group, cyano group, nitro group, hydroxyl group, acyloxy group, amino group, a lower alkylsulfonylamino group, acylamino group, a lower alkoxycarbonylamino group, acyl group, mercapto group, a lower alkylthio group, a lower alkylsulfinyl group or a lower alkylsulfonyl group (more preferably hydrogen, a lower alkoxy group, aralkyloxy group, a lower alkoxy lower alkoxy group, hydroxyl group or acyloxy group), and, among them, those of the above formula wherein $R^{2'}$ and $R^{5'}$ are hydrogen are preferable, and further preferable ones are those represented by the following formula:

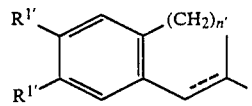

wherein the broken line designates possible presence of a double bond (more preferably the presence of a double bond), $R^{1'}$ stands for a lower alkoxy group (more preferably methoxy or ethoxy), and n' denotes an integer of 1 to 4 (more preferably 2 or 3).

Examples of the lower alkyl group shown by $R^1$, $R^2$ or $R^3$ include alkyl groups, the carbon number of which ranges from about 1 to about 4, such as methyl group, ethyl group, propyl group, etc. $R^1$, $R^2$ and $R^3$ may be the same or different from one another, while it is preferable that $R^1$, $R^2$ and $R^3$ are all methyl group.

Preferable examples of X are the methylene group or carbonyl group.

In the above-mentioned formula (I), the substituent group G is bonded to the 2- or 3-position of the piperazine ring. In the groups in which G represents $-(CH_2)_n-Z-R^6$, examples of the lower alkyl group shown by $R^6$ include alkyl groups, whose carbon number ranges from about 1 to about 4, such as methyl, ethyl, propyl, isopropyl, butyl, isobutyl, sec-butyl, tert-butyl, etc.

Examples of the lower halo alkyl group shown by $R^6$ include halo alkyl groups in which the alkyl group, whose carbon number ranges from about 1 to about 4, is substituted with about 1 to 3 halogen atoms, (e.g. F, Cl, Br, etc.), such as trifluoromethyl, 2,2,2-trifluoroethyl, difluoromethyl, etc.

Examples of the lower alkenyl group shown by $R^6$ include alkenyl groups, whose carbon number ranges from about 2 to about 4, such as 2-propenyl, 2-butenyl, 2-methyl-2-propenyl, etc.

Examples of the lower alkynyl group shown by $R^6$ include alkynyl groups, whose carbon number ranges from about 2 to about 4, such as ethynyl, 2-propynyl, 2-butynyl, etc.

Examples of the lower cycloalkyl group shown by $R^6$ include cycloalkyl groups, whose carbon number ranges from about 3 to about 6, such as cyclopropyl, cyclobutyl, cyclopentyl, cyclohexyl, cyclopropylmethyl, etc.

Referring to the above-mentioned formula (I), in the groups of the formula $-(CH_2)_n-Z-R^6$ shown by G, when Z is $CONR^7$ or $NR^7$, examples of the lower alkyl group, the lower halo alkyl group and the lower alkenyl group shown by the above-mentioned $R^6$, and examples of the lower alkoxycarbonyl group shown by $R^7$ include an alkoxycarbonyl group, the carbon number of the alkoxy moiety of which ranges from about 1 to about 4, such as methoxycarbonyl, ethoxycarbonyl, propoxycarbonyl and butoxycarbonyl. $R^6$ and $R^7$ may be the same or different from one another, and $R^6$ and $R^7$ may be combined so that

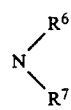

forms a 5- or 6-membered ring (e.g. pyrrolidine, piperidine, etc.).

Referring to the above-mentioned formula (I), among the groups of $-(CH_2)_n-Z-R^6$ shown by G, preferable ones are those wherein Z stands for O, COO or CONR$^7$ (R$^7$ stands for hydrogen or a lower alkyl (more preferably methyl or ethyl)) and R$^6$ stands for hydrogen or a lower alkyl (more preferably methyl or ethyl).

Among the compounds represented by the above-mentioned formula (I) [compounds (I)]those represented by the following formula (I') or pharmaceutically acceptable acid addition salts thereof are preferable:

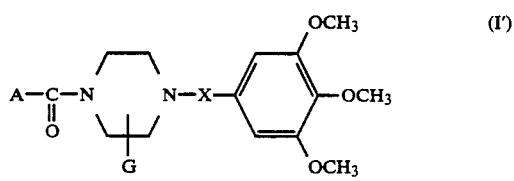

wherein X stands for a methylene group or carbonyl group; A stands for a phenyl group substituted with 2 to 3 lower alkoxy groups (more preferably methoxy or ethoxy), a heterocyclic group represented by the formula:

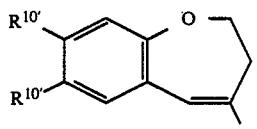

wherein R$^{10'}$ stands for a lower alkoxy group (more preferably methoxy or ethoxy), or a condensed polycyclic hydrocarbon group represented by the formula:

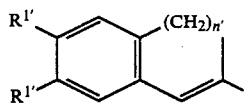

wherein n' denotes an integer of 2 or 3; and R$^{1'}$ stands for a lower alkoxy group (more preferably methoxy or ethoxy); G stands for the formula $-(CH_2)_n-Z-R^6$ wherein n denotes an integer of 0 to 2; Z stands for O, COO, or CONR$^7$ (wherein R$^7$ stands for hydrogen or a lower alkyl group (more preferably methyl or ethyl)); and R$^6$ stands for hydrogen or a lower alkyl (more preferably methyl or ethyl).

The compound (I) may form a salt with an inorganic acid such as hydrogen chloride, hydrogen bromide, sulfuric acid, nitric acid, phosphoric acid, etc. or an organic acid such as acetic acid, tartaric acid, citric acid, fumaric acid, maleic acid, toluenesulfonic acid, methanesulfonic acid, etc., or may form a quaternary salt with, for example, a lower alkyl halide, the carbon number of the alkyl moiety of which ranges from about 1 to about 4, (e.g. methyl iodide, ethyl iodide, propyl iodide). As the salts of the compound (I), pharmaceutically acceptable ones are preferable, and pharmaceutically acceptable acid addition salts are more preferable. Hydrates of the compound (I) are also usable.

The compound (I) of the present invention can be prepared by, for example, subjecting a compound represented by the formula: A-COOH (II) wherein A is of the same meaning as defined above and a compound represented by the formula:

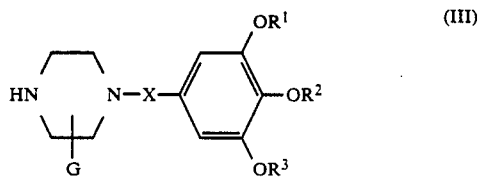

wherein each symbol is of the same meaning as defined above to dehydrative condensation.

The dehydrative condensation can be conducted by, for example, a conventional reaction for forming an amido-bond. More concretely stating, the dehydrative condensation is carried out by using singly an amide-forming reagent such as dicyclohexylcarbodiimide, N,N'-carbonyldiimidazole, diphenyl phosphoryl azide, diethyl phosphorocyanidate, etc.; or by allowing a compound (II) to react with a compound (III), after converting the compound (II) to an active ester by subjecting a phenol such as 2,4,5-trichlorophenol, pentachlorophenol, pentafluorophenol, 2-nitrophenol or 4-nitrophenol, etc., or an N-hydroxy compound such as N-hydroxysuccinimide, 1-hydroxybenztriazole, N-hydroxypiperidine, N-hydroxy-5-norbornene-2,3-dicarboxyimide, etc. to condensation in the presence of a catalyst such as dicyclohexylcarbodiimide, etc.; or by allowing a compound (II) to react with a compound (III), after converting the compound (II) to a mixed acid anhydride by allowing it to react with an acid chloride such as ethyl chlorocarbonate, isobutyl chlorocarbonate, benzyl chlorocarbonate, etc. This amide-bond-forming reaction can be accelerated, in either case of allowing a compound (II) to react directly with a compound (III) or allowing a compound (II) to react with a compound (III) after converting the former to its active ester or mixed acid anhydride, by the addition of preferably an organic base such as a tertiary amine (e.g. triethylamine, N-methylpiperidine). The reaction temperature ranges from about $-20°$ C. to about $+50°$ C., preferably from about $-10°$ C. to about $+25°$ C. Examples of the solvent usually employed include dioxane, tetrahydrofuran, acetonitrile, pyridine, N,N-dimethylformamide, N,N-dimethylacetamide, dimethylsulfoxide, N-nethylpyrrolidone, chloroform, methylene chloride, etc., and these may be used singly or as a suitable mixture.

The compound (I) of the present invention can also be prepared by, for example, allowing a compound represented by the formula: A—COW (IV), wherein A is of the same meaning as defined above and W stands for a halogen atom, to react with a compound (III). This reaction can be allowed to proceed usually in the presence or absence of water or an organic solvent (e.g. acetonitrile, dimethylformamide, dimethylacetamide, dimethylsulfoxide, tetrahydrofuran, benzene, toluene, ethyl acetate, chloroform, methylene chloride), by keeping the temperature range from about $-20°$ C. to about 150° C. In this case, for the purpose of accelerating the reaction rate, a base such as potassium carbonate, sodium hydroxide, sodium hydrogen-carbonate, pyridine, triethylamine, etc. can be allowed to be present in the reaction system.

The compound (I) of the present invention can also be prepared by allowing a compound represented by the formula:

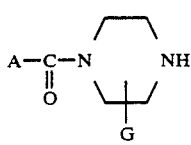
(V)

wherein A and G are of the same meaning as defined above to react with a compound represented by the formula:

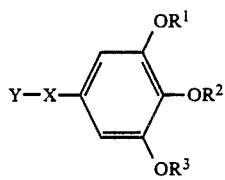

[VI] wherein $R^1$, $R^2$, $R^3$ and X are of the same meaning as defined above; Y stands for halogen (X : methylene group or carbonyl group) or a group represented by the formula: $R^aSO_2$—O— (wherein $R^a$ stands for a lower(-$C_{1-4}$) alkyl, trifluoromethyl, phenyl or p-tolyl) (X : methylene group). The reaction can be allowed to proceed in water or in an organic solvent (e.g. acetonitrile, dimethylformamide, dimethylacetamide, dimethylsulfoxide, tetrahydrofuran, acetone, methyl ethyl ketone, benzene, toluene) singly or in an admixture thereof, while keeping the temperature to range from about −20° C. to about +150° C. In this case, a base such as potassium carbonate, sodium hydroxide, potassium hydroxide, pyridine, triethylamine, etc. can be allowed to be present in the reaction system.

The compound (I) of the present invention, wherein X is carbonyl group, can be prepared by, for example, subjecting a compound (V) and a compound represented by the formula:

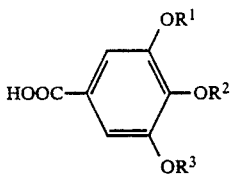

wherein R1, R2 and R3 are of the same meaning as defined above to dehydrative condensation. This dehydrative condensation reaction can be conducted in a manner similar to that of the compound (II) and the compound (III).

And, the compound (I) of the present invention, wherein X is methylene group, can also be prepared by, for example, subjecting a compound (V) and a compound represented by the formula:

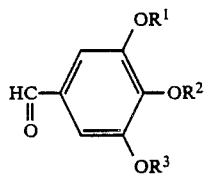

wherein $R_1$, $R_2$ and $R_3$ is of the same meaning as defined above to condensation under reductive conditions.

As the reductive conditions, mention is made of, for example, catalytic reduction using as the catalyst a metal such as platinum, palladium Raney nickel, rhodium, etc. or a mixture of the metal and an optional carrier (e.g. carbon); reduction by means of metallic hydride such as lithium aluminium hydride, lithium borohydride, lithium cyanoborohydride, sodium borohydride, sodium cyanoborohydride, etc.; reduction by means of metallic sodium, metallic magnesium, etc. and alcohols; reduction by means of a metal such as iron, zinc, etc. and an acid such as hydrochloric acid, acetic acid, etc.; electrolytic reduction; reduction by means of reductase; etc. The above-mentioned reaction is usually carried out in the presence of water or an organic solvent (e.g. methanol, ethanol, ethylether, dioxane, methylene chloride, chloroform, benzene, toluene, acetic acid, N,N-dimethylformamide, N,N-dimethylacetamide), and the reaction temperature varies with the reduction process employed, but, in general, preferably ranges from about −20° C. to about 100° C. This reaction can attain the purpose satisfactorily by carrying it out under normal pressure, but it may be conducted, depending on convenience, under elevated or reduced pressure.

The compound (I), wherein G is —$CH_2ZR^6$ (Z=O, COO or CONH, and $R^6$=a lower alkyl group, a lower halo alkyl group or a lower alkenyl group), can be prepared by, subjecting, for example, a compound (IX) represented by the formula:

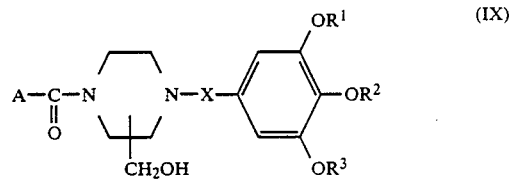
(IX)

wherein A, X, $R^1$, $R^2$, and $R^3$ are of the same meaning as defined above and a compound represented by the formula: Y'—$R^6$ (X)

wherein Y' stands for a halogen atom or a group represented by the formula $R^aSO_2$—O— (wherein $R^a$ stands for a lower ($C_1$-$C_4$)alkyl, trifluoromethyl phenyl or p-tolyl), a group represented by the formula —COW (wherein W stands for halogen atom), the formula $R^6$COOCO— or the formula NCO—, and $R^6$ stands for a lower alkyl group, a lower halo alkyl group or a lower alkenyl group to condensation.

The condensation is carried out by allowing the compound (IX) to react with the compound (X) in an aprotonic solvent (e.g. dimethylsulfoxide, tetrahydrofuran, toluene, acetonitrile, N,N-dimethylformamide, methylene chloride, etc.).

In the case that Y' of the compound (X) is a halogen atom or $R^a$—$SO_2$—O— ($R^a$ of the same meaning as defined above), the reaction between the compounds (IX) and (X) is an alkylation, and the reaction can be accelerated by adding a base such as sodium hydride, sodium amide, silver oxide or n-butyl lithium. The reaction proceeds usually within a temperature range from −20° C. to +150° C.

In the case that Y' of the compound (X) is —COW or $R^6$COOCO—, the reaction between the compound (IX) and the compound (X) is acylation, and the reaction can be accelerated by adding a base such as triethylamine, 4-dimethyl aminopyridine, sodium hydrogencarbonate, potassium carbonate, etc. The reaction proceeds usually within a temperature range from −20° C. to 150° C.

In the case that Y' of the compound (X) is NCO—, the reaction proceeds even without addition of a catalyst, but the reaction can be further accelerated by adding a base such as triethylamine, pyridine or 4-dimethyl aminopyridine. The reaction temperature preferably ranges from about −20° C. to about +150° C.

The compound (I), wherein G is —CH$_2$ZR$^6$ (Z=O, S, NR$^7$ (R$^7$ is of the same meaning as defined above), and R$^6$ is hydrogen, a lower alkyl group, a lower halo alkyl group or a lower alkenyl group), can also be prepared by subjecting for example the compound (XI) represented by the formula:

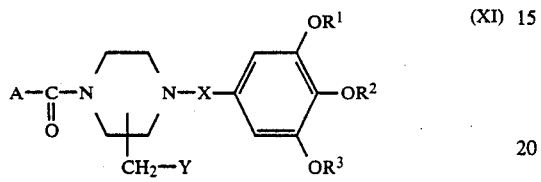

(XI)

wherein A, X, R$^1$, R$^2$, R$^3$ and Y are of the same meaning as defined above to substitution with the compound (XII) represented by the formula: HZR$^6$ (XII) wherein Z is O, S, NR$^7$ (R$^7$ is of the same meaning as defined above), and R$^6$ is of the same meaning as defined above.

The substitution reaction can be carried out, in a non-protonic solvent (e.g. dimethylsulfoxide, dioxane, tetrahydrofuran, toluene, acetonitrile, N,N-dimethylformamide, methylene chloride, etc.), by allowing an inorganic base such as sodium hydride, sodium amide, silver oxide, sodium hydrogencarbonate, potassium carbonate, sodium hydroxide, potassium hydroxide, etc., or an organic base such as triethylamine, pyridine, 4-N,N-dimethyl aminopyridine, etc. to coexist, as a desalting agent, as a desalting agent, in the reaction system for the purpose of acceleration of the reaction. The reaction temperature usually ranges from −20° C. to +150° C.

The intended compound (I) of the present invention thus obtained can be isolated from the reaction mixture by a conventional separating and purifying means e.g. extraction, concentration, neutralization, filtration, recrystallization, column chromatography, thin-layer chromatography, etc.

In the compound (I), at least two stereoisomers can exist. These isomers, singly or a mixture thereof, are of course included in the scope of the present invention, and, when desired, these isomers can be prepared individually. For example, by conducting the above-mentioned reaction using a single isomer of the starting compounds (III), (V), (IX) and (XI), a single optical isomer of the compound (I) can be obtained. And, when the product is a mixture of two or more isomers, it can be separated into the respective isomers by a conventional separating means, for example, causing formation of a salt with an optically active acid (e.g. camphor sulfonic acid, tartaric acid, dibenzoyl tartaric acid, etc.) or an optically active base (e.g. cinchonine, cinchonidine, quinine, quinidine, α-methylbenzylamine, dehydroabiethylamine, etc.), various kinds of chromatography, fractional recrystallization, etc.

The starting compounds (II), (III), (V), (IX) and (XI) can be easily produced by processes shown by, for example, the following reaction scheme.

The compound (II) can easily be synthesized by utilizing compounds disclosed in known literature references or in accordance with methods described in the following literature references [e.g. Jacques et al, Bull. Soc. Chim. Fr., 512 (1950); Hashem et al., J. Med. Chem., 19, 229(1976); Itoh et al., Chem. Pharm. Bull., 26, 504 (1978); Miyake et al., Chem. Pharm. Bull., 31, 2329 (1983); Itoh et al., Chem. Pharm. Bull, 32, 130 (1984); Tamura et al., J. Agr. Chem. Soc. Japan, 27, 318 (1953); Organic Syntheses, 26, 28 (1946)] or methods analogous thereto. For example, when the compound (II) is a compound represented by the formula:

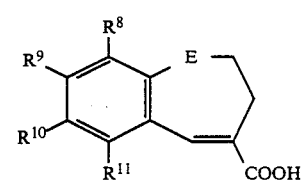

wherein E stands for O, S or CH$_2$; R$^8$, R$^9$, R$^{10}$, and R$^{11}$ respectively stand for substituents defined in the above-mentioned A, it can easily be synthesized in accordance with the following reaction schema.

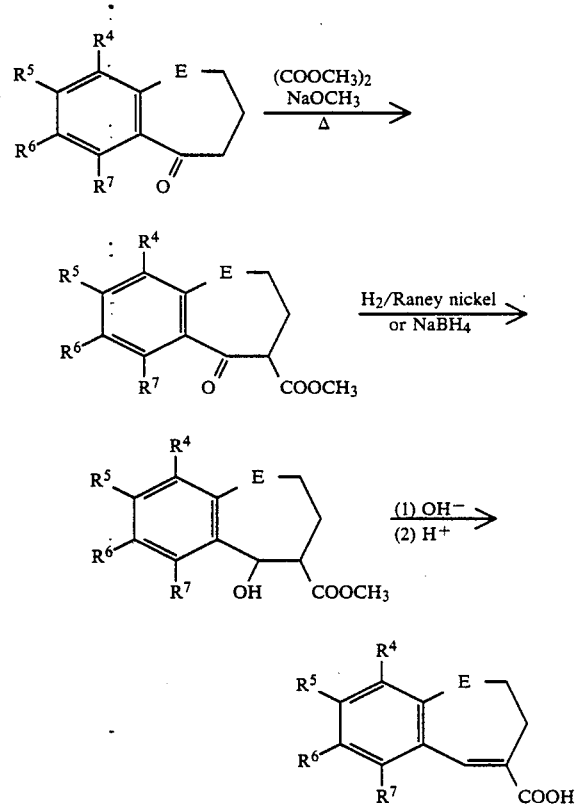

And, the starting compounds (III), (V), (IX) and (XI) can easily be synthesized by, for example, the following reactions.

Further, in the reaction schema shown below, Ph stands for phenyl group, Boc stands for tert-butyloxycarbonyl group, and A, G, X, Y, R$^1$, R$^2$, R$^3$, R$^6$ and R$^a$ are of the same meaning as defined above.

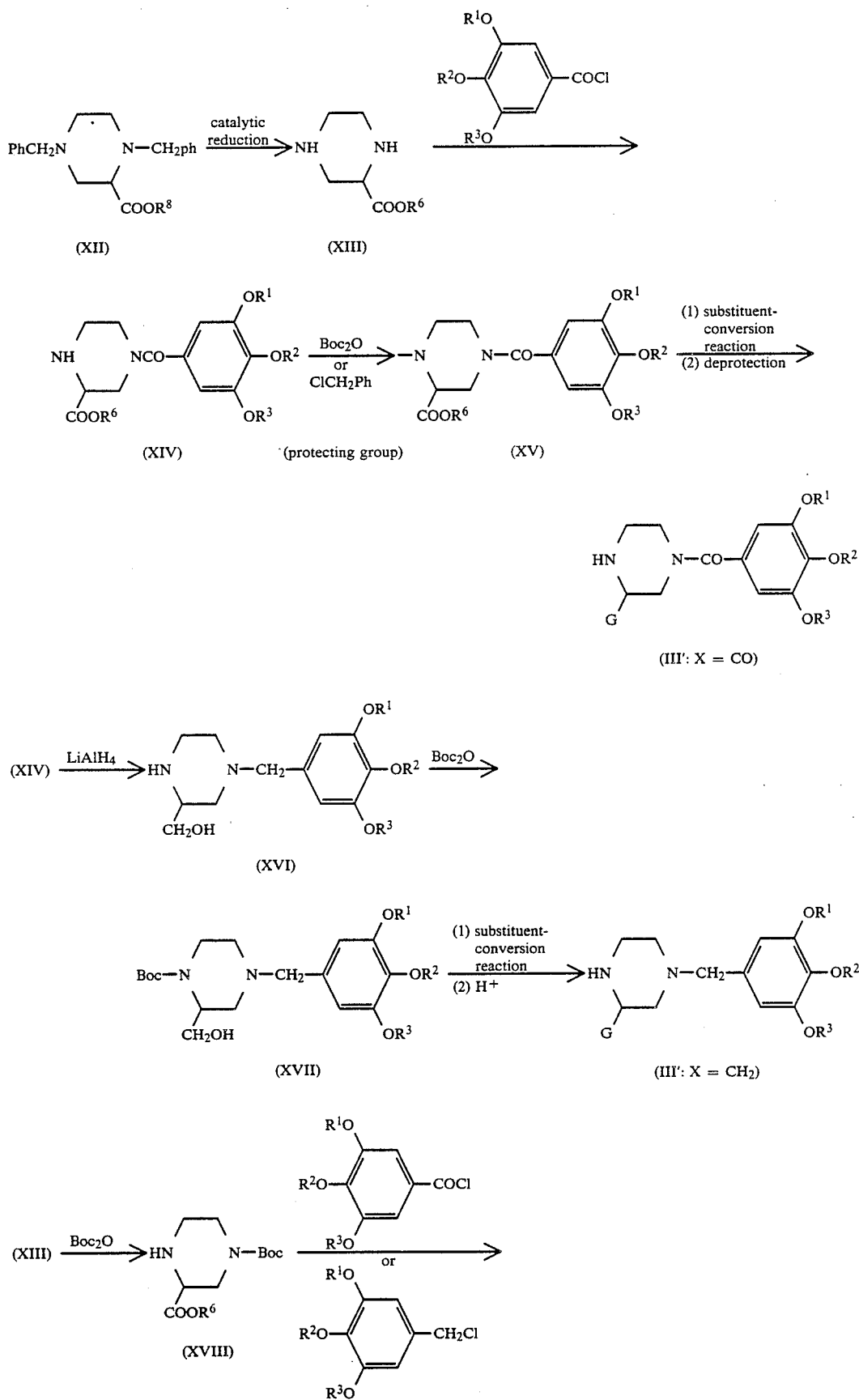

-continued
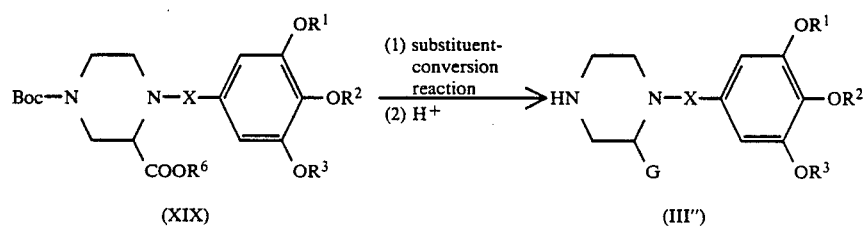
(XIX) → (III″)
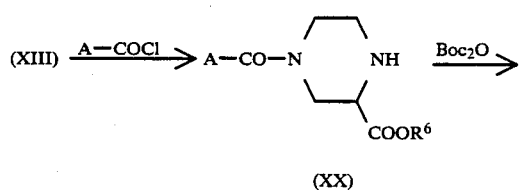
(XIII) → (XX)
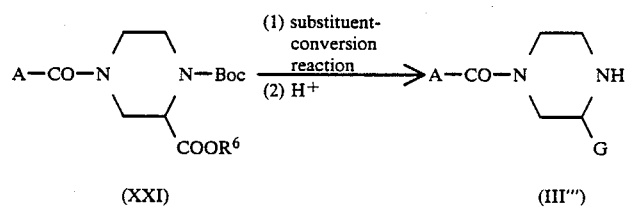
(XXI) → (III‴)
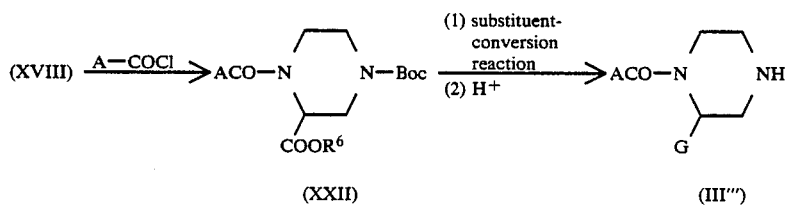
(XVIII) → (XXII) → (III‴)
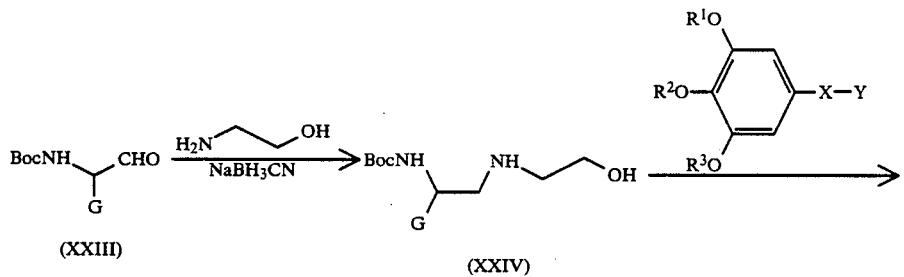
(XXIII) → (XXIV)
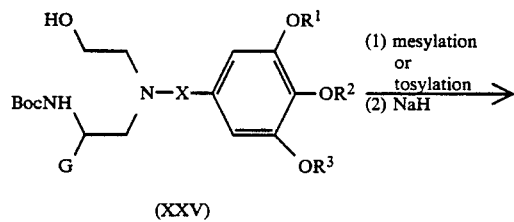
(XXV)
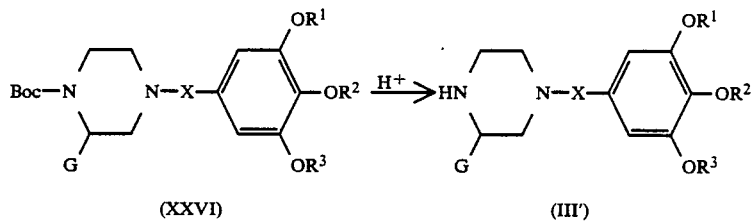
(XXVI) → (III′)

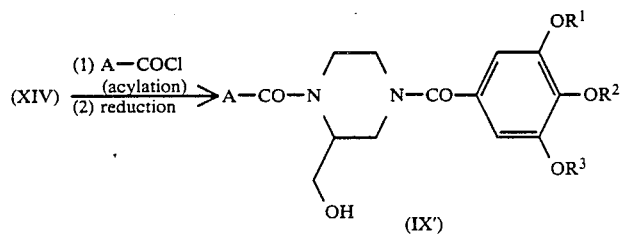
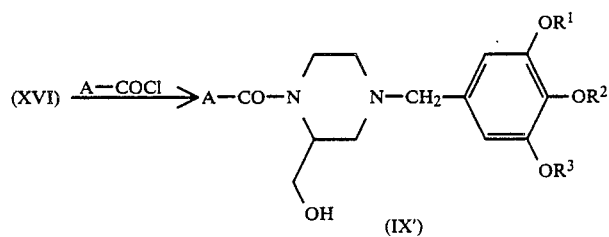
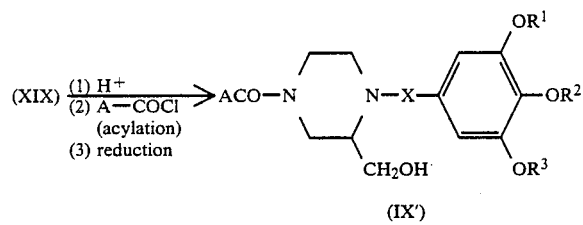
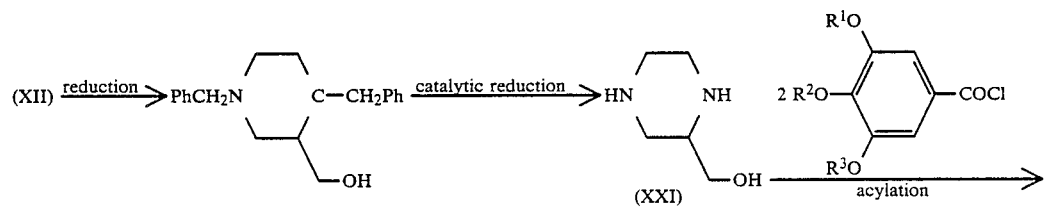
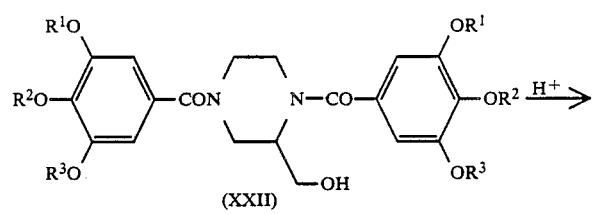
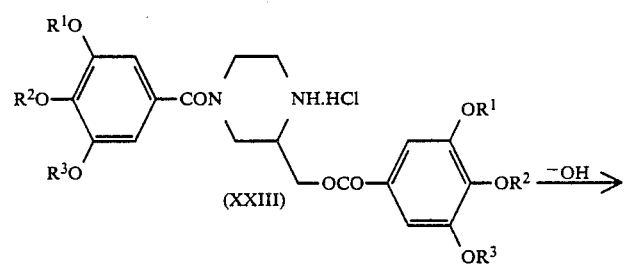
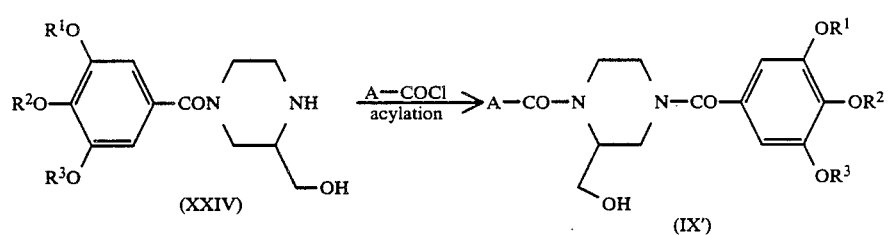

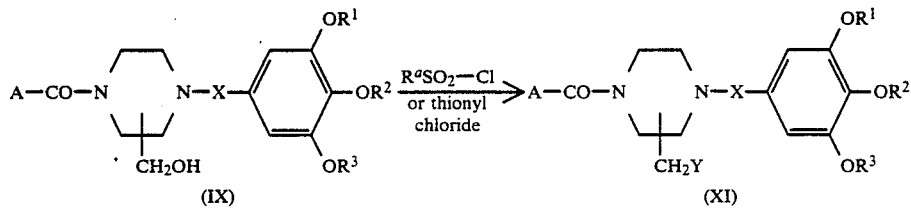

On the method of producing the compound (III) shown by the above-mentioned reaction schema, explanation in further detail is given as follows. As the starting materials, (XII) and (XIII)($R^6$=$C_2H_5$) disclosed in a known literature reference, E. Jucker and E. Rissi, Helv. Chim. Acta, 45, 2383 (1962) can be employed. By allowing (XIII) to react with one equivalent of acid chloride or acid anhydride (tert-butyl dicarbonate) as a desalting agent in the presence of, for example, triethylamine, (XIV), (XVIII) and (XX) are obtained. As the reaction solvent, use is made of an aprotonic solvent such as methylene chloride, acetonitrile, tetrahydrofuran, etc. The reaction temperature ranges from $-20°$ C. to $+100°$ C., preferably from about $-20°$ C. to $+30°$ C. The amino group of (XIV) thus obtained is protected, by a conventional means, with tert-butyloxycarbonyl group or benzyl group to convert (XIV) into (XV), then the ester group of (XV) is, upon necessity, subjected to substituent-conversion reaction. Examples of this substitution-conversion reaction include, among others, 1) hydrolysis of ester group, followed by amidation of the carboxyl group obtained, 2) reduction of ester group to alcohol by using $NaBH_4$, $LiBH_4$, $LiAlH_4$, 3) alkylation of the hydroxyl group of the hydroxy compound obtained (modification similar to the alkylation of (IX) with (X)), and 4) the hydroxy compound obtained is subjected to mesylation or tosylation, followed by substitution with a nucleophilic reagent (e.g. amines, mercaptans) (reaction similar to substitution reaction of (XI) by using (XII)). Then, deprotection of the protecting group, tert-butyloxycarbonyl group (Boc group) can be carried out by using hydrogen chloride in a solvent such as ethyl acetate, methanol, ethanol, acetic acid, etc., or by using trifluoroacetic acid or trifluoromethanesulfonic acid in acetic acid. And, in the case that the protecting group is a benzyl group, deprotection is performed by catalytic reduction. The reaction temperature ranges from $-20°$ C. to $+150°$ C., and, usually the end-product can be obtained usually at room temperatures.

The reaction of (XIV)→(XVI) is the reduction of an amido group and ester group, and as the reducing agent, use is made of $LiAlH_4$, $NaAlH_2(OCH_2CH_2OCH_3)_2$, etc. As the solvent, use is made of dioxane, tetrahydrofuran, toluene, benzene, ethyl ether, etc., and the reaction proceeds at temperatures ranging from $-20°$ C. to $+100°$ C. The reaction of (XVII)→(III') (X=$CH_2$) after tert-butyloxycarbonylation of (XVII) can be conducted in a manner similar to that of (XV)→(III')(X 32 CO). The reaction of (XVIII)→(XIX) is an acylation or alkylation of amino group, and the acylation can be conducted under conditions similar to those in (XIII)→(XIV), (XVIII) and (XX). The alkylation can be conducted by allowing (XVIII) to react with, for example, 3,4,5-trimethoxybenzyl chloride in an organic solvent such as methylene chloride, tetrahydrofuran, acetonitrile, N,N-dimethylformamide, toluene, etc. at temperatures ranging from $-20°$ C. to $+150°$ C. In this case, the reaction can be accelerated by allowing an organic base such as triethylamine, pyridine, 4-N,N-dimethylaminopyridine, etc. or an inorganic base such as sodium carbonate, potassium carbonate, sodium hydrogencarbonate, etc. to coexist in the reaction system as a de-salting agent. The reaction of (XIX)→(III'') can be conducted in a manner similar to that of (XV)→(III')(X=CO). (XIII)→(XX) is a reaction similar to that of (XIII)→(XIV), then the (XX) is subjected to tert-butyloxycarbonylation to give (XXI), and the reaction of (XXI)→(III''') is similar to (XV)→(III')(X=CO).

The reaction of (XVIII)→(XXII)→(III''') can be conducted by acylation similar to that in (XIII)→(XIV), followed by a reaction similar to that of (XV)→(III'). (X=CO).

And, the compound (III') can be derived by employing, as the starting material, the compound (XXIII) derived from an amino acid (cf. e.g. Y. Hamada, M. Shibata, T. Sugiura, S. Kato and T. Shioiri, J Org. Chem., 52, 1252 (1987)). The reaction of (XXIII)→(XXIV) is the reductive amination of a carbonyl group, and the compound (XXIV) can be produced by subjecting the compound (XXIII) and ethanolamine to condensation under reductive conditions in methanol, ethanol, acetonitrile, tetrahydrofuran, etc. singly or a mixture thereof.

The reduction can be conducted by catalytic reduction using, as the catalyst, a metal such as Raney nickel, palladium, rhodium, etc. or a mixture of the metal and a suitable carrier, or reduction using a metal hydride such as lithium cyanoborohydride ($LiBH_3CN$), sodium cyanoborohydride ($NaBH_3CN$), sodium borohydride ($NaBH_4$). The reaction temperature varies with the means of reduction employed, but ranges preferably from about $-20°$ C. to about $+100°$ C. The reaction of (XXIV)→(XXV) can be conducted under conditions of acylation or alkylation similar to those in the reaction of (XVIII)→(XIX). The reaction of (XXV)→(XXVI) can be performed by allowing (XXV) to react with methanesulfonyl chloride or p-toluene-sulfonyl chloride in a non-protonic solvent such as methylene chloride, tetrahydrofuran, acetonitrile, etc. in the co-presence of a base such as triethylamine, sodium hydrogencarbonate, followed by subjecting the reaction mixture to ring-closure reaction.

The said ring-closure reaction can be performed by using, as the de-salting agent, sodium hydride, lithium hydride, etc. Preferable reaction solvents include a non-polar solvent such as tetrahydrofuran, acetonitrile, N,N-dimethylformamide, etc. The reaction temperature ranges from about $-20°$ C. to about $+100°$ C. By subjecting (XXVI) to a reaction for elimination of the protecting group, it can be led to (III'). Acylation step of (XIV)→(IX'), (XVI)→(IX'), (XIX)→(IX'), (XXI)→(XX), and (XXIV)→(IX') can be performed under conditions similar to the case of (XIII)→(XIV).

The reduction step in (XIV)→(IX'), (XIX)→(IX'), and (XII)→(XX) reduces the ester group to alcohol and is performed by heating in a mixture solvent of tetrahydrofuran and methanol using, for example, sodium borohydride (NaBH$_4$) as the reducing agent, or by allowing the reaction to proceed in ethanol at room temperature using lithium borohydride as the reducing agent.

The step of (IX)→(XI), when Y stands for e.g. halogen, can be performed by allowing (IX) to react with thionyl chloride in a solvent such as methylene chloride, toluene, ethyl acetate, etc. at temperatures ranging from −20° C. to +50° C. in the presence of a base such as triethylamine. And, when Y stands for R$^a$SO$_2$—O—, the above step can be performed by using, for example, methanesulfonyl chloride in place of thionyl chloride under similar conditions.

(Action)

The compound (I) and salts thereof exhibit excellent PAF antagonism and are useful as prophylactic and therapeutic agents for circulatory disturbances due to PAF, for example, thrombosis, apoplexy (e.g. cerebral hemorrahge, cerebral thrombosis), myocardial infarction, angina pectoris, venous thrombosis, nephritis (e.g. gluomerulonephritis), diabetic nephritides, shock (e.g. endotoxin shock observed after grave infectious diseases or postoperative shock, intravascular hemagglutination syndrome caused by endotoxin, anaphylactic shock, hemorrhagic shock); gastroenteric diseases caused by PAF (e.g. gastric ulcer); diseases associated with allergy and inflammation (e.g. bronchial asthma, psoriasis); pneumonia; rejection symptoms associated with increase in the amount of PAF produced in the case of internal organ transplantation; insufficiency of internal organs (e.g. heart, liver, kidney) in the case of internal organ operation. Further, compound (I) and salts thereof are useful for prophylaxis and therapy of diseases induced by succorhea of endothelin (hyperendothelin symptoms) having a strong action of vasoconstriction and contraction of smooth muscle and trachea [M. Yanagisawa et al., Nature, 332, 411 (1988)], for instance hypertension or bronchial stenosis, etc. caused by endothelin [Y. Uchida et al., Eur. J. Pharmacol., 154, 227(1988)], and ischemic cerebral and cardiac diseases (e.g. apoplexy, angina pectoris, myocardial infarction, cardiac insufficiency, arrhythmia), renal disorders (e.g. nephritis), circulatory insufficiency of various organs (e.g. liver, lung, intestine), asthma, etc. associated with a higher concentration (about 0.1 to 5 n mol./100 ml of blood) of endothelin. The compound (I) and salts thereof are low in toxicity, and can therefore be administered orally or non-orally as they are in the form of powder or as a pharmaceutical composition in a suitable dosage form, to mammals (e.g. man, rabbit, dog, cat, rat, mouse). The dosage varies depending upon the subject and disease to be treated, conditions thereof and route of administration, and when the compound (I) or a salt thereof is used for prophylaxis or therapy of shock in a human adult, it is convenient to administer through intravenous injection usually in a single dose in the range of from about 0.01 to about 20 mg body weight, preferably in the range of from about 0.1 to about 10 mg/kg body weight, more preferably in the range of from about 0.1 to about 2 mg/kg body weight, about once to five times a day, preferably about once to three times a day. And, the compound (I) or a salt thereof can also be administered through drip injection in a single dose in the range of from about 0.01 to about 1.0 mg/kg body weight/min. for about one hour, about once to five times a day, preferably once to three times a day. The dosages for other non-oral routes as well as the oral dosage may be selected referring to the above-mentioned dose levels. When shock symptoms are very serious, dosage may be increased depending on the symptoms.

And, when the compound (I) or a salt thereof is used orally for prophylaxis or therapy of, for example, thrombosis, bronchial asthma, nephritis, etc. in a human adult, it is convenient to administer usually in a single dose in the range of from about 0.05 to about 20 mg/kg body weight, preferably in the range of from about 0.2 to about 5 mg/kg body weight, about once to five times, preferably from once to three times. The dosages for other non-oral routes may be selected referring to the above-mentioned dose levels.

The pharmaceutical composition to be used for the above administration comprises an effective amount of the compound (I) or a salt thereof and a pharmaceutically acceptable carrier or excipient, and the said composition is provided in a dosage form suitable for oral or non-oral administration.

The composition for oral administration includes, for example, solid or liquid dosage forms, and as their examples, there may be mentioned tablets (inclusive of sugar-coated tablets and film-coating tablets), pills, granules, powders, capsules (inclusive of soft capsules), syrups, emulsions, suspensions, etc. Such compositions can be manufactured by per se known procedures and comprise carriers and excipients commonly used in the pharmaceutical industry. Examples of the carriers and excipients for the preparation of tablets include lactose, starch, sugar, magnesium stearate, etc.

The compositions for non-oral administration include, for example, injections, suppositories, ointments, fomentations, paints, etc., and as examples of injectables, there may be mentioned dosage forms, such as injectable solutions for intravenous injection, for subcutaneous injection, for intracutaneous injection, for intramuscular injection, for drip injection, etc. Such injectable solutions are prepared by per se known procedures, for example, by dissolving suspending or emulsifying the compound (I) or a salt thereof in a sterile aqueous or oily solution usually employed for injectable solutions. The aqueous solution for injection includes, for example, physiological saline solution isotonic solution containing glucose and other adjuvants, and it may be used in combination with a suitable solubilizer, such as alcohols (e.g. ethanol), polyalcohols (e.g. propylene glycol, polyethylene glycol), and nonionic surface active agents [e.g. Polysorbate 80, HCO-50 (polyoxyethylene (50 mol.) adduct of hydrogenated castor oil)], etc. The oily solution includes, for example, sesame oil, soybean oil, etc., and may be used in combination with a solubilizer e g. benzyl benzoate, benzyl alcohol, etc. The injectable solution prepared is usually filled into suitable ampoules to be supplied as injectable preparations. The suppositories for rectal administration are prepared by a per se known procedure, for example, by incorporating the compound (I) or a salt thereof into a conventional base material for suppository use, followed by moulding.

Incidentally, the above-mentioned compositions may contain any other active components, so long as they do not cause undesirable interactions by the incorporation with the compound (I) or a salt thereof. For example, to mammals suffering from infectious diseases, an antibiotic may be administered together with the compound (I) or a salt thereof for preventing endotoxin-shock.

EXAMPLES

The present invention is illustrated more specifically by the following Reference Examples and Working Examples, but is not limited thereto.

REFERENCE EXAMPLE 1

To a mixture of ethyl piperazine-2-carboxylate dihydrochloride (2.0 g), triethylamine (1.2 ml) and dichloromethane (40 ml) is added dropwise, under ice-cooling while stirring, a solution of 3,4,5-trimethoxybenzoyl chloride (1.85 g) in dichloromethane (25 ml). The mixture is stirred for one hour, then the reaction mixture is poured into ice-water, followed by extraction with methylene chloride. The organic layer is washed with water, dried and concentrated under reduced pressure. The residue is purified by means of a silica gel column chromatography (eluent : ethyl acetate-acetone-hexane=2:1:2) to afford ethyl 4-(3,4,5-trimethoxybenzoyl)-piperazine-2-carboxylate (2.5 g). This product is recrystallized from ethyl acetatehexane to give colorless crystals, m.p. 114–115° C.

Elemental Analysis for $C_{17}H_{24}N_2O_6$:
Calcd.: C 57.94; H 6.86; N 7.95:
Found : C 57.83; H 6.91; N 7.79:

REFERENCE EXAMPLE 2

A solution of 3,4,5-trimethoxybenzoyl chloride (10.9 g) in dichloromethane (100 ml) is added dropwise taking one hour, under ice-cooling while stirring, to a mixture of methyl piperazine-2-carboxylate dihydrochloride (10.24 g), triethylamine (18.7 g) and dichloromethane (200 ml). The reaction mixture is poured into ice-water, followed by extraction with dichloromethane. The organic layer is washed with water, dried and the solvent is distilled off under reduced pressure. Crystals obtained from the residue are recrystallized from ethyl acetate and hexane to afford methyl 4-(3,4,5-trimethoxybenzoyl)piperazine-2-carboxylate (9.6 g) as colorless needles, m.p. 113–114° C.

Elemental Analysis for $C_{16}H_{22}N_2O_6$:
Calcd.: C 56.80; H 6.55; N 8.28:
Found : C 56.72; H 6.68; N 8.43:

REFERENCE EXAMPLE 3

A solution of di-tert-butyl dicarbonate (4.6 g) in dichloromethane (15 ml) is added dropwise taking 15 minutes, while stirring at room temperature, to a mixture of methyl 4-(3,4,5-trimethoxybenzoyl)piperazine-2-carboxylate (5.0 g) obtained in Reference Example 1, triethylamine (2.2 g) and dichloromethane (50 ml). The reaction mixture is stirred for 2 hours at room temperature, followed by concentration under reduced pressure. The concentrate is subjected to extraction with ethyl acetate. The organic layer is washed with water and dried, then the solvent is distilled off under reduced pressure. Crystals obtained from the residue are recrystallized from ethyl acetate to afford methyl 1-tert-butoxycarbonyl-4-(3,4,5-trimethoxybenzoyl)piperazine-2-carboxylate (6.3 g) as colorless needles, m.p. 163–164° C.

Elemental Analysis for $C_{21}H_{30}N_2O_8$:
Calcd.: C 58.05; H 6.90; N 6.39:
Found : C 57.98; H 6.82; N 6.48:

REFERENCE EXAMPLE 4

Methanol (6 ml) is added dropwise taking 30 minutes under reflux by heating, while stirring, to a mixture of methyl 1-tert-butoxycarbonyl-4-(3,4,5-trimethoxybenzoyl)piperazine-2-carboxylate (6.3 g), sodium borohydride (1.64 g) and tetrahydrofuran (80 ml). The reaction mixture is poured into water, followed by extraction with ethyl acetate. The organic layer is washed with water and dried, then the solvent is distilled off. Crystals obtained from the residue are recrystallized from ethyl acetate-ether to afford 1-tert-butoxycarbonyl-4-(3,4,5-trimethoxybenzoyl)piperazine-2-methanol (4.15 g) as colorless crystals, m.p. 119–120° C.

Elemental Analysis for $C_{20}H+N_2O_7$:
Calcd.: C 58.52; H 7.37; N 6.82:
Found : C 58.46; H 7.48; N 6.70:

REFERENCE EXAMPLE 5

To a mixture of 1-tert-butoxycarbonyl-4-(3,4,5-trimethoxybenzoyl)piperazine-2-methanol (12.0 g), methyl iodide (21.3 g) and dimethyl formamide (50 ml) is added, under ice-cooling while stirring, in limited amounts, 60% sodium hydride (1.8 g). The mixture is stirred for 30 further minutes, and the reaction mixture is poured into ice-water, followed by extraction with ethyl acetate. The organic layer is dried and concentrated. The residue is purified by means of a silica gel column chromatography (eluent: dichloromethane-ethyl acetate=1:1) to afford 1-tert-butoxycarbonyl-2-methoxymethyl-4-(3,4,5-trimethoxybenzoyl)piperazine (12.5 g) as colorless crystals, m.p. 127° C.

Elemental Analysis for $C_{21}H_{32}N_2O_7$:
Calcd.: C 59.42; H 7.60; N 6.60:
Found : C 59.29; H 7.61; N 6.52:

REFERENCE EXAMPLE 6

To 3N HCl-ethyl acetate solution (50 ml) is added 1-tert-butoxycarbonyl-2-methoxymethyl-4-(3 4 5trimethoxybenzoyl)piperazine (12.0 g), and the mixture is stirred for one hour at room temperature. Resulting precipitates are collected by filtration and washed with ether to give 2-methoxymethyl-4-(3,4,5-trimethoxybenzoyl)piperazine hydrochloride (10.5 g) as colorless crystals, m.p. 210–215° C.

Elemental Analysis for $C_{16}H_{24}N_2O_5 \cdot HCl$:
Calcd.: C 53.26; H 6.98; N 7.76:
Found : C 53.36; H 6.89; N 7.53:

REFERENCE EXAMPLE 7

To a mixture of methyl 1-tert-butoxycarbon-vl-4(3,4,5-trimethoxybenzoyl)piperazine-2-carboxylate (500 mg), methanol (3 ml) and water (3 ml) is added sodium hydroxide (100 mg), which is stirred for 30 minutes at room temperature. The reaction mixture is poured into a 5% aqueous solution of citric acid, followed by extraction with dichloromethane. The organic layer is dried and then concentrated to give a crude product, which is recrystallized from ethyl acetate to afford 1-tert-butoxycarbonyl-4-(3,4,5-trimethoxy-benzoyl)piperazine-2-carboxylic acid (400 mg) as colorless crystals, m.p. 188–190° C.

Elemental Analysis for $C_{16}H_{24}N_2O_5 \cdot HCl$:
Calcd.: C 56.60; H 6.65; N 6.60:
Found : C 56.26; H 6.63; N 6.47:

REFERENCE EXAMPLE 8

To a mixture of 1-tert-butoxycarbonyl-4-(3,4,5-trimethoxybenzoyl)piperazine-2-carboxylic acid (3.0 g), N-hydroxysuccinimide (1.2 g) and dioxane (30 ml) is added, at room temperature, dicyclohexyl carbodiimide (2.6 g). The mixture is stirred for 5 hours. To a mixture of dimethylamine hydrochloride (8.0 g), triethylamine (10.0g) and dioxane (30 ml) is added dropwise at 0° C the solution of active ester prepared above. The reaction mixture is concentrated, and the concentrate is dissolved in dichloromethane. The solution is washed with a 5% aqueous solution of citric acid and a saturated aqueous solution of sodium hydrogencarbonate, which is then dried and further concentrated. The crude product is subjected to a silica gel column chromatography (ethyl acetate-methanol=9:1) to afford N,N-dimethyl 1-tert-butoxycarbonyl-4-(3,4,5-trimethoxybenzoyl)piperazine-2carboxamide (2.1 g) as colorless crystals, m.p. 146–147° C.

Elemental Analysis for $C_{22}H_{33}N_3O_7$:
Calcd.: C 58.52; H 7.37; N 9.31:
Found : C 58.40; H 7.45; N 9.20:

REFERENCE EXAMPLE 9

A mixture of N,N-dimethyl 1-tert-butoxycarbonyl-4(3,4,5-trimethoxybenzoyl)piperazine-2-carboxamide (2.0 g) and 3N HCl - ethyl acetate (20 ml) is stirred for 30 minutes at room temperature. The reaction mixture is concentrated, and the concentrate is poured into a saturated aqueous solution of potassium carbonate, followed by extraction with dichloromethane. The organic layer is dried and concentrated to afford N,N-dimethyl 4-(3,4,5-trimethoxybenzoyl)piperazine-2-carboxamide (1.5 g) as colorless crystals, m.p. 167–168° C.

Elemental Analysis for $C_{17}H_{25}N_3O_5$:
Calcd.: C 58.11; H 7.17; N 11.96:
Found : C 58.22; H 7.17; N 12.03:

REFERENCE EXAMPLE 10

A mixture of ethyl 4-(3,4,5-trimethoxybenzoyl)-piperazine-2-carboxylate obtained in Reference Example 1 (1.0 g), benzyl chloride(0.54 g), potassium carbonate (0.8 g) and acetonitrile (12 ml) is heated under reflux for 5 hours while stirring. The reaction mixture is poured into ice-water, followed by extraction with ethyl acetate.

The organic layer is washed with water and dried, then the solvent is distilled off under reduced pressure. The residue is purified by means of a silica gel column chromatography (hexane:ethyl acetate:acetone=2:1:1) to afford ethyl 1-benzyl-4(3,4,5-trimethoxybenzoyl)piperazine-2-carboxylate as a colorless oily product (1.2 g). This product is led to hydrochloride and recrystallized from ethanol to give colorless crystals, m.p. 162–165° C.

Elemental Analysis for $C_{24}H_{30}N_2O_6 \cdot HCl$ :
Calcd.: C 60.18; H 6.52: N 5.85:
Found : C 60.09; H 6.44; N 5.80:

REFERENCE EXAMPLE 11

To a solution of ethyl 1-benzyl-4-(3,4,5-trimethoxybenzoyl)piperazine-2-carboxylate (0.4 g) obtained in Reference Example 10 in tetrahydrofuran (15 ml) is added sodium borohydride (0.1 g). To the mixture is added dropwise methanol (2 ml) taking 30 minutes under reflux by heating while stirring. The reaction mixture is concentrated under reduced pressure and then poured into water, followed by extraction with ethyl acetate. The organic layer is washed with water and dried, then the solvent is distilled off under reduced pressure. The residue is purified by means of a silica gel column chromatography (acetone:ethyl acetate:hexane=2 2:1), and the resultant crystals are recrystallized from ethyl acetate and hexane to afford 1-benzyl-4-(3,4,5-trimethoxydibenzoyl)piperazine-2-methanol (0.24 g) as colorless needles, m.p. 84–85° C.

Elemental Analysis for $C_{22}H_{28}N_2O_5$:
Calcd.: C 65.98; H 7.05; N 7.00:
Found : C 65.73; H 6.96; N 6.99:

REFERENCE EXAMPLE 12

In N,N-dimethylformamide (2 ml) is dissolved 1-benzyl-4-(3,4,5-trimethoxybenzoyl)piperazine-2-methanol (1.0 g). The solution is added dropwise to a mixture of sodium hydride (0.15 g) and N,N-dimethylformamide (4 ml) taking 5 minutes at 0 ° C while stirring. To the mixture is further added ethyl iodide (0.5 g) at 0° C., followed by stirring for 30 minutes at room temperature. The reaction mixture is poured into icewater and extracted with ethyl acetate. The organic layer is washed with water and dried, then the solvent is distilled off under reduced pressure to afford 1-benzyl-2-ethoxymethyl-4-(3,4,5trimethoxybenzoyl)piperazine as a colorless oily product (1.0 g). This product is led to its hydrochloride, followed by recrystallization from acetone to give colorless needles, m.p. 130–132° C.

Elemental Analysis for $C_{24}H_{32}N_2O_5 \cdot HCl \times 1/2H_2O$:
Calcd.: C 60.81; H 7.23; N 5.91:
Found : C 60.68; H 7.45; N 5.72:

REFERENCE EXAMPLE 13

In methanol (15 ml) is dissolved 1-benzyl-2-ethoxymethyl-4-(3,4,5-trimethoxybenzoyl)piperazine hydrochloride (1.0 g) obtained in Reference Example 12. To the solution is added 10% palladium-carbon (0.3 g), and the mixture is stirred for 3 hours in hydrogen streams. The reaction mixture is subjected to filtration, and the filtrate is subjected to distillation under reduced pressure to leave crystals, followed by recrystallization from ethanol-ether to afford 3-ethoxymethyl-1-(3,4,5-trimethoxybenzoyl)piperazine hydrochloride (0.8 g) as colorless crystals, m.p 203–204° C.

Elemental Analysis for $C_{17}H_{26}N_2O_5 \times HCl \times 1/2 H_2O$:
Calcd.: C 53.19; H 7.35; N 7.30:
Found : C 53.42; H 7.25; N 7.31:

REFERENCE EXAMPLE 14

To a suspension of lithium aluminum hydride (0.3 g) in ether (12 ml) is added, dropwise taking 15 minutes at room temperature while stirring, a solution of 3-methoxymethyl 1-(3,4,5-trimethoxybenzoyl)piperazine (2.1 g) obtained in Reference Example 6 in tetrahydrofuran (10 ml). The reaction mixture is stirred at 40 ° C for one hour. To the mixture cooled to 0 ° C are added water (0.3 ml), a 15% aqueous solution of sodium hydroxide (0.3 ml) and water (1 ml) successively to cause hydrolysis, then insolubles are filtered off. The filtrate is concentrated under reduced pressure, and the concentrate is dissolved in dilute HCl, followed by extraction with ethyl acetate. The aqueous layer is neutralized with sodium hydrogencarbonate, and extracted with dichloromethane. The organic layer is washed with water and dried, then the solvent is distilled off under reduced pressure to give 3-methoxymethyl-1-(3,4,5-trimethoxybenzyl)piperazine as a colorless oily product (1.4 g). This product is converted to its hydrochloride, followed by recrystallization from ethanol and ether to afford colorless needles, m.p. 162–165° C.

Elemental Analysis for $C_{16}H_{26}N_2O_4 \times 2HCl \times 1/2-H_2O$:
Calcd.: C 48.98; H 7.45; N, 7.14:
Found : C 49.27; H 7.36; N, 6.97:

REFERENCE EXAMPLE 15

A solution of 2,3-dimethoxy-6,7-dihydro-5H-benzocycloheptene-8-carbonyl chloride (2.14 g) in dichloromethane (20 ml) is added dropwise, taking 40 minutes while stirring at 0° C., to a mixture of methyl piperazine-2-carboxylate hydrochloride (1.75 g), triethylamine (3.2 g) and dichloromethane (40 ml). The reaction mixture is poured into ice-water and shaken. The organic layer is separated and subjected to distillation under reduced pressure. The residue is dissolved in 1N-HCl (20 ml) and washed with ethyl acetate. The aqueous layer is separated and then neutralized with sodium hydrogencarbonate, followed by extraction with dichloromethane. The organic layer is dried, and the solvent is distilled off. Crystals obtained from the residue are recrystallized from ethyl acetate - hexane to afford methyl 4-(2,3-dimethoxy-6,7-dihydro-5H-benzocyclohepten-8-ylcarbonyl)piperazine-2carboxylate as colorless needles (2.45 g), m.p. 103–104° C.

Elemental Analysis for $C_{20}H_{26}N_2O_5$:
Calcd.: C 64.15; H 7.00; N 7.48:
Found : C 64.03; H 7.02; N 7.34:

REFERENCE EXAMPLE 16

A solution of di-tert-butyl dicarbonate (5.0 g) in dichloromethane (30 ml) is added dropwise, taking one hour at 0° C. while stirring, to a mixture of methyl piperazine-2-carboxylate dihydrochloride (5.0 g), triethylamine (7 g) and dichloromethane (70 ml). The reaction mixture is poured into ice-water and extracted with dichloromethane. The organic layer is washed with water and dried, then the solvent is distilled off under reduced pressure. The residue is purified by means of a silica gel column chromatography (eluent, dichloromethane:acetone :ethanol =5:5:1) to afford methyl 4-tert-butoxycarbonylpiperazine-2-carboxylate as a colorless oily product (4.9 g).

Elemental Analysis for $C_{11}H_{20}N_2O_4$:
Calcd.: C 54.08; H 8.25; N 11.47:
Found : C 54.46; H 8.38; N 11.22:

REFERENCE EXAMPLE 17

A solution of 2,3-dimethoxy-6,7-dihydro-5H-benzocycloheptene-8-carbonyl chloride (1.6 g) in dichloromethane (15 ml) is added dropwise, at 0° C. taking 3 minutes, to a mixture of 4-tert-butoxycarbonylpiperazine-2-carboxylate (1.8 g) obtained in Reference Example 16, triethylamine (1.3 g) and dichloromethane (20 ml). The reaction mixture is poured into water and extracted with dichloromethane. The organic layer is washed with water and dried, then the solvent is distilled off under reduced pressure. The residue is purified by means of a silica gel column chromatography (hexane:ethyl acetate:acetone=5:4:1) to afford methyl 1-(2,3-dimethoxy-6,7-dihydro-5H-benzocyclohepten-8-ylcarbonyl)-4-tert-butoxycarbonylpiperazine-2-carboxylate as a colorless oily product (2.8 g).

Elemental Analysis for $C_{25}H_{34}N_2O_7$:
Calcd.: C 63.27; H 7.22; N 5.90:
Found : C 63.56; H 7.36; N 5.71:

REFERENCE EXAMPLE 18

To a solution of 4.5N HCl-ethyl acetate solution (10 ml) is added methyl 1-(2,3-dimethoxy-6,7-dihydro-5H-benzocyclohepten-8-ylcarbonyl)-4-tert-butoxycarbonylpiperazine-2-carboxylate (1.7 g). The reaction mixture is left standing at room temperature for 5 hours. Then the solvent is distilled off under reduced pressure. To the residue is added ethyl ether. Resulting precipitates are collected and dried to afford methyl 1-(2,3-dimethoxy-6,7-dihydro-5H-benzo-cyclohepten-8-ylcarbonyl}piperazine-2-carboxylate hydrochloride as colorless powder (1.2 g).

Elemental Analysis for $C_{20}H_{26}N_2O_5 \times HCl \times 1/2H_2O$
Calcd.: C 57.21; H 6.72; N 6.67:
Found : C 57.17; H 6.93; N 6.42:

REFERENCE EXAMPLE 19

A mixture of methyl 4-(tert-butoxycarbonyl)piperazine-2-carboxylate (3.5 g) obtained in Reference Example 16, 3,4,5-trimethoxybenzyl chloride (4.6 g), potassium carbonate (6.0 g) and acetonitrile (80 ml) is refluxed by heating for 10 hours while stirring. The reaction mixture is concentrated under reduced pressure. The concentrate is added to water and extracted with ethyl acetate. The organic layer is washed with water and dried, then the solvent is distilled off under reduced pressure. The residue is purified by means of a silica gel column chromatography (hexane:ethyl acetate =3:2) to afford methyl 4-tert-butoxycarbonyl-1-(3,4,5-trimethoxy-benzyl)piperazine-2-carboxylate as a colorless oily product (5.2 g).

Elemental Analysis for $C_{21}H_{32}N_2O_7$:
Calcd.: C 59.41; H 7.60; N 6.60:
Found : C 59.18; H 7.83; N 6.34:

REFERENCE EXAMPLE 20

In 4.5N HCl-ethyl acetate solution (20 ml) is dissolved methyl 4-tert-butoxycarbonyl-1-(3,4,5-trimethoxybenzyl)piperazine-2-carboxylate (5.0 g) obtained in Reference Example 19, and the solution is left standing at room temperature for 5 hours. The reaction mixture is concentrated under reduced pressure to give crystalline methyl 1-(3,4,5-trimethoxybenzyl)-piperazine-2-carboxylate dihydrochloride (4.3 g). This product is recrystallized from ethanol to afford colorless needles, m.p. 170–175° C.

Elemental Analysis for $C_{16}H_{24}N_2O_5 \times 2HCl \times 1/2-H_2O$:
Calcd.: C 47.30; H 6.70; N 6.89:
Found : C 47.16; H 6.89; N 6.83:

REFERENCE EXAMPLE 21

A solution of N-benzyloxycarbonyloxy-5-norbornene-2,3-dicarboxyimide (1.44 g) in dichloromethane (10 ml) is added dropwise, taking 20 minutes while stirring under ice-cooling, to a mixture of methyl piperazine-2carboxylate dihydrochloride (1.0 g), triethylamine (1.4 g) and dichloromethane (12 ml). The reaction mixture is stirred for 30 minutes, and then poured into water, followed by extraction with dichloromethane. The organic layer is washed with water and dried, then the solvent is distilled off under reduced pressure. The residue is purified by means of a silica gel column chromatography (acetone: dichloromethane:hexane=3:2:1) to afford methyl 4-benzyloxycarbonylpiperazine-2-carboxylate as a colorless oily product (1.2 g).

Elemental Analysis for $C_{14}H_{18}N_2O_4$:

Calcd.: C 60.42; H 6.52; N 10.07:
Found : C 60.18; H 6.79; N 10.46:

REFERENCE EXAMPLE 22

A mixture of methyl 4-benzyloxycarbonylpiperazine-2-carboxylate (1.2 g) obtained in Reference Example 21, triethylamine (0.9 g) and dichloromethane (15 ml) is added dropwise, taking 5 minutes while stirring at 0° C., to a solution of 3,4,5-trimethoxybenzoyl chloride (1.08 g) in dichloromethane (10 ml). The reaction mixture is stirred at room temperature for 10 minutes, and then poured into water, followed by extraction with dichloromethane. The organic layer is washed with water and dried, then the solvent is distilled off under reduced pressure. The residue is purified by means of a silica gel column chromatography (hexane:ethyl acetate:acetone=2:2:1) to give methyl 4-benzyloxycarbonyl-1-(3,4,5-trimethoxybenzoyl)-piperazine-2-carboxylate as a colorless oily product (2.1 g).

Elemental Analysis for $C_{24}H_{28}N_2O_8$:
Calcd.: C 61.01; H 5.97; N 5.93:
Found : C 61.39; H 6.28; N 5.73:

REFERENCE EXAMPLE 23

A mixture of 4-benzyloxycarbonyl-1-(3,4,5-trimethoxybenzoyl)piperazine-2-carboxylate (2.0 g) obtained in Reference Example 22, methanol (30 ml) and 10% palladium-carbon (0.5 g) is stirred for one hour at room temperature in hydrogen streams. The reaction mixture is subjected to filtration, and the filtrate is subjected to distillation under reduced pressure to give methyl 1-(3,4,5-trimethoxybenzoyl)piperazine-2-carboxylate (1.05 g) as colorless crystals. Recrystallization of this product from ethyl acetate-hexane affords colorless needles, m.p. 134–135° C.

Calcd.: C 56.80; H 6.55; N 8.28:
Found : C 56.58; H 6.63; N 8.06:

REFERENCE EXAMPLE 24

A solution of di-tert-butyl dicarbonate (3.79 g) in dichloromethane (15 ml) is added dropwise, taking 5 minutes at 0 ° C while stirring, to a mixture of methyl 4-(benzyloxycarbonyl)piperazine-2-carboxylate (4.4 g) obtained in Reference Example 21, triethylamine (4 g) and dichloromethane (40 ml). The reaction mixture is stirred at room temperature for 2 hours. To the mixture is added water, followed by extraction with dichloromethane. The organic layer is washed with water and dried, then the solvent is distilled off under reduced pressure. The residue is purified by means of a silica gel column chromatography (hexane:ethyl acetate=2:1) to afford methyl 4-benzyloxycarbonyl-1-(tert-butoxycarbonyl)piperazine-2carboxylate (5.5 g) as a colorless oily product.

Elemental Analysis for $C_{19}H_{26}N_2O_6$:
Calcd.: C 60.30; H 6.93; N 7.40:
Found : C 60.12; H 7.18; N 7.15:

REFERENCE EXAMPLE 25

A mixture of methyl 4-benzyloxycarbonyl-1-(tert-butoxycarbonyl)piperazine-2-carboxylate (5.4 g) obtained in Reference Example 24, 10% palladium-carbon (1.2 g) and methanol (60 mM) is stirred at room temperature for 4 hours in hydrogen streams. The reaction mixture is subjected to filtration, and the filtrate is subjected to distillation under reduced pressure to afford methyl 1-(tert-butoxycarbonyl)-piperazine-2-carboxylate as a pale yellow oily product (3.3 g).

Elemental Analysis for $C_{11}H_{20}N_2O_4$:
Calcd.: C 54.09; H 8.25; N 11.47:
Found : C 53.86; H 8.49; N 11.18:

REFERENCE EXAMPLE 26

A mixture of methyl 1-(tert-butoxycarbonyl)piperazine-2-carboxylate (3.2 g) obtained in Reference Example 25, 3,4,5-trimethoxybenzyl chloride (3.5 g), potassium carbonate (4.0 g) and acetonitrile (80 ml) is refluxed by heating for 6 hours while stirring. The reaction mixture is concentrated under reduced pressure, and then extracted with ethyl acetate. The organic layer is washed with water, dried, and then the solvent is distilled off. The residue is purified by means of a silica gel column chromatography (hexane:ethyl acetate =3:2). Resulting crystals are recrystallized from ethyl acetate and hexane to afford 1-tert-butoxycarbonyl-4-(3,4,5trimethoxybenzyl) piperazine-2-carboxylate (3.0 g) as 35 colorless needles, m.p. 113–114° C.

Elemental Analysis for $C_{21}H_{32}N_2O_7$:
Calcd.: C 59.42; H 7.60; N 6.60:
Found : C 59.49; H 7.67; N 6.39:

REFERENCE EXAMPLE 27

Methyl 1-tert-butoxycarbonyl-4-(3,4,5-trimethoxybenzyl)piperazine-2-carboxylate (3.0 g) obtained in Reference Example 26 is dissolved in 4.5N HCl-ethyl acetate solution (15 ml), and the solution is stirred for 3 hours at room temperature. The reaction mixture is concentrated under reduced pressure, and the resulting crystals are recrystallized from ethanol to afford methyl 4-(3,4,5-trimethoxybenzyl)piperazine-2carboxylate (2.5 g) as colorless needles, m.p. 155–160° C.

Elemental Analysis for $C_{16}H_{24}N_2O_5 \times 2HCl \times H_2O$:
Calcd.: C 46.27; H 6.80; N 6.75:
Found : C 46.49; H 6.64; N 6.58:

REFERENCE EXAMPLE 28

To a mixture of 3.4M solution of sodium bis(2-methoxyethoxy)aluminum hydride (50.0 g) in toluene (250 ml) is added dropwise, taking one hour at room temperature while stirring, a solution of ethyl 4(3,4,5-trimethoxybenzoyl) piperazine-2-carboxylate (17.6 g) in toluene (100 ml). Excess amount of the reducing agent is decomposed with a 40% aqueous solution of sodium hydroxide, then inorganic substances are filtered off, and the filtrate is concentrated under reduced pressure. The concentrate is recrystallized from methanol to afford 4-(3,4,5-trimethoxybenzyl) piperazine-2-methanol (10.5 g) as colorless crystals, m.p. 93° C.

Elemental Analysis for $C_{15}H_{24}N_2O_4$:
Calcd.: C 60.79; H 8.16; N 9.45:
Found : C 60.77; H 8.06; N 9.18:

REFERENCE EXAMPLE 29

A solution of 2,3-dimethoxy-6,7-dihydro-5H-benzocycloheptene-8-carbonylchloride (1.1 g) in dichloromethane (12 ml) is added dropwise, taking 30 minutes while stirring under ice-cooling, to a mixture of ethyl piperazine-2-carboxylate hydrochloride (1.0 g), triethylamine (0.5 g) and dichloromethane (20 ml). The reaction mixture is stirred for one hour at 0 ° C, and then poured into ice-water, followed by extraction with dichloromethane. The organic layer is washed with water and dried, then the solvent is distilled off under reduced pressure. The residue is purified by means of a silica gel column chromatography (hexane:ethyl acetate:acetone=1:1:1) to afford ethyl 4-(2,3-dimethoxy-6,7-dihydro-5H-benzocyclohepten-8-ylcarbonyl)piperazine-2-carboxylate as crystals (1.2 g). This product is recrystallized form ethyl acetate and hexane to give colorless prisms, m.p. 105–106° C.

Elemental Analysis for $C_{21}H_{28}N_2O_5$:
Calcd.: C 64.93; H 7.27; N 7.21:
Found : C 64.89; H 7.32; N 7.13:

REFERENCE EXAMPLE 30

To a solution of oxalyl chloride (3.09 g) in methylene chloride (50 ml) is added dropwise at −78° C. a solution of dimethyl sulfoxide (2.86 g) in methylene chloride (20 ml). The mixture is stirred for 10 minutes. To the resulting reaction mixture is added dropwise a solution of 1-tertbutoxycarbonyl-4-(3,4,5-trimethoxybenzoyl)piperazine-2-methanol (5.0 g) obtained in Reference Example 4 in methylene chloride (10 ml). The mixture is stirred for 20 minutes. To the mixture is added triethylamine (7.4 g), followed by raising the reaction temperature up to room temperature. The reaction mixture is poured into ice water, followed by extraction with methylene chloride. The organic layer is washed with water, dried and concentrated under reduced pressure. The concentrate is recrystallized from ethyl acetate to give 1-tert-butoxycarbonyl-4-(3,4,5-trimethoxybenzoyl)piperazine-2-carbaldehyde as colorless prisms (4.1 g), m.p. 160–161° C.

Elemental Analysis for $C_{20}H_{28}N_2O_7$:

Calcd.: C, 58.81; H, 6.91; N, 6.86:
Found : C, 58.42; H, 7.01; N, 6.75:

REFERENCE EXAMPLE 31

A mixture of 1-tert-butoxycarbonyl-4-(3,4,5-trimethoxybenzoyl)piperazine-2-carbaldehyde (3.8 g) obtained in Reference Example 30, carbethoxymethylenetriphenylphosphorane (3.9 g) and toluene (30 ml) is stirred at 50° C for 3 hours. The reaction mixture is concentrated under reduced pressure, and the concentrate is purified by means of a silica gel column chromatography (eluent : ethyl acetate) to give ethyl 1-tert-butoxycarbonyl-4-(3,4,5-trimethoxybenzoyl)-2-piperazine acrylate as a colorless oily product (4.0 g). This product is dissolved in ethanol (40 ml). To the solution is added 10% Pd-carbon (400 mg), and the mixture is stirred at room temperature for 8 hours in hydrogen streams. The catalyst is filtered off and the filtrate is concentrated under reduced pressure The concentrate is dissolved in ethyl acetate (10 ml), to which is added 4.5N HCl-ethyl acetate (30 ml), and the mixture is stirred for 3 hours at room temperatures. Precipitating crystals are dried to give ethyl 4(3,4,5-trimethoxybenzoyl)-2-piperazine propionatehydrochloride as colorless crystals (2.5 g), m.p. 182–184° C.

Elemental Analysis for $C_{19}H_{28}N_2O_6 \times HCl$:
Calcd.: C 54.74; H, 7.01; N, 6.72:
Found : C 54.53; H, 7.04; N, 6.57:

REFERENCE EXAMPLE 32

To a mixture of ethyl 4-(3,4,5-trimethoxybenzoyl)2-piperazine propionate hydrochloride obtained in Reference Example 31 (1.3 g), triethylamine (315 mg) and toluene (10 ml) is added dropwise, while stirring, at room temperature a 3.4M toluene solution of sodium bis(2-methoxyethoxy)aluminum hydride (Red-Al®) (9 g). To the reaction mixture, after stirring for 3 hours, is added water, followed by extraction with ethyl acetate. The organic layer is washed with water, dried and concentrated under reduced pressure. The concentrate is led to its hydrochloride, which is recrystallized from ethanol to give 4-(3,4,5-trimethoxybenzyl)-2piperazine propanol dihydrochloride as colorless crystals (1 0 g) m.p. 212–215° C.

Elemental Analysis for $C_{17}H_{28}N_2O_4 \times 2HCl$:
Calcd.: C 51.39; H, 7.61; N, 7.05:
Found : C 51.29; H, 7.78; N, 6.91:

WORKING EXAMPLE 1

A solution of 2,3-dimethoxy-6,7-dihydro-5H-benzocycloheptene-8-carbonyl chloride (370 mg) in dichloromethane (10 ml) is added dropwise, taking 30 minutes under ice-cooling, to a mixture of methyl 4(3,4,5-trimethoxybenzoyl)piperazine-2-carbonylate (400 mg) obtained in Reference Example 2, triethylamine (1 ml) and dichloromethane (50 ml). The reaction mixture is washed with an aqueous solution of citric acid and an aqueous solution of sodium hydrogencarbonate, and dried over magnesium sulfate, followed by concentration. The concentrate is subjected to a silica gel column chromatography (eluent: ethyl acetate-methanol =97:3) to afford methyl 1-(2,3-dimethoxy6,7-dihydro-5H-benzocyclohepten-8-ylcarbonyl) -4-(3,4,5trimethoxybenzoyl)piperazine-2-carboxylate (450 mg) as colorless crystals, m.p. 134° C.

Elemental Analysis for $C_{30}H_{36}N_2O_9 \times 1/2H_2O$:
Calcd.: C 62.38; H 6.46; N 4.85:
Found : C 62.30; H,6.31; N 4.80:

WORKING EXAMPLE 2

A solution of 2,3-dimethoxy-6,7-dihydro-5H-benzocycloheptene-8-carbonyl chloride (400 mg) in dichloromethane (10 ml) is added dropwise, taking 30 minutes under ice-cooling, to a mixture of N,N-dimethyl 4-(3,4,5-trimethoxybenzoyl)piperazine-2-carboxamide (500 mg) obtained in Reference Example 9, triethylamine (1 ml) and dichloromethane (50 ml). The reaction mixture is washed with a 5% aqueous solution of citric acid and a saturated aqueous solution of $NaHCO_3$, dried and then concentrated under reduced pressure. The concentrate is subjected to a silica gel column chromatography (eluent: ethyl acetate) to afford N,N-dimethyl 1-(2,3-dimethoxy-6,7-dihydro-5H-benzocyclohepten-8-ylcarbonyl) -4-(3,4 5trimethoxybenzoyl)piperidine-2-carboxamide (430 mg) as colorless crystals, m.p. 190–191° C.

Elemental Analysis for $C_{31}H_{39}N_3O_8$:
Calcd.: C 64.01; H 6.76; N 7.22:
Found : C 63.83; H 6.95; N 7.01:

WORKING EXAMPLES 3 to 6

In a manner corresponding to Working Example 2, N,N-dimethyl 4-(3,4,5-trimethoxybenzoyl)piperazine-2-carboxamide is allowed to react with a corresponding acid chloride to afford compounds of Working Examples 3 to 6.

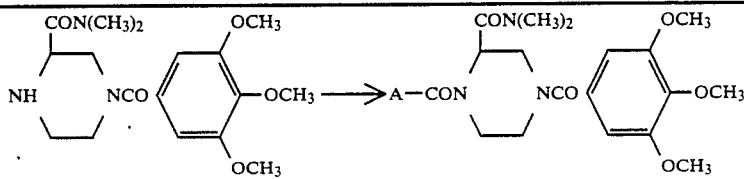

| Ex. No. | A | Molecular Formula | Elemental Analysis Calcd. (Found) | | | m.p. (°C.) |
|---|---|---|---|---|---|---|
| | | | C | H | N | |
| 3 | H₃CO, H₃CO (bicyclic with O) | C₃₀H₃₇N₃O₉ | 61.74 (61.61) | 6.39 (6.38) | 7.20 (7.17) | 167–168 |
| 4 | H₃CO, H₃CO-phenyl-propenyl | C₂₈H₃₅N₃O₈ | 62.10 (61.95) | 6.51 (6.54) | 7.76 (7.92) | 196 |
| 5 | H₃CO, butoxy-phenyl-propenyl | C₃₁H₄₁N₃O₈ | 63.79 (63.58) | 7.08 (7.15) | 7.20 (7.16) | 118 |
| 6 | H₃CO, H₃CO, OCH₃ trimethoxyphenyl-methyl | C₂₇H₃₅N₃O₈ | 59.44 (59.33) | 6.47 (6.51) | 7.70 (7.59) | 205–206 |

WORKING EXAMPLE 7

A solution of 7,8-dimethoxy-2,3-dihydro-1-benzoxepine-4-carbonyl chloride (300 mg) in dichloromethane (10 ml) is added dropwise, taking 30 minutes under ice-cooling while stirring, to a mixture of 3-methoxymethyl-1-(3,4,5-trimethoxybenzoyl)piperazine × hydrochloride (400 mg) obtained in Reference Example 6, triethylamine (1 ml) and dichloromethane (30 ml). The reaction mixture is washed with an aqueous solution of citric acid and an aqueous solution of sodium hydrogencarbonate, then dried over magnesium sulfate, followed by concentration. The concentrate is subjected to a silica gel column chromatography (eluent: ethyl acetate-methanol =95:5) to afford 1-(7,8-dimethoxy2,3-dihydro-1-benzoxepin-4-ylcarbonyl) -2-methoxymethyl4-(3,4,5-trimethoxybenzoyl)piperazine (520 mg) as colorless crystals, m.p. 142° C.

Elemental Analysis for C₂₉H₃₆N₂O₉ × 1/2H₂O:
Calcd.: C 61.58; H 6.59; N 4.95:
Found : C 61.54; H 6.49; N 4.89:

WORKING EXAMPLES 8 to 18

In a manner similar to Working Example 7, 3-methoxymethyl-1-(3,4,5-trimethoxybenzoyl)piperazine is allowed to react with a corresponding acid chloride to afford compounds of Working Examples 8 to 18.

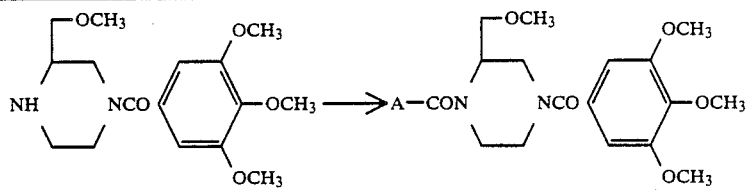

| Ex. No. | A | Molecular Formula | Elemental Analysis Calcd. (Found) | | | m.p. (°C.) |
|---|---|---|---|---|---|---|
| | | | C | H | N | |
| 8 | H₃CO, H₃CO-tetrahydronaphthyl | C₂₈H₃₆N₂O₈ | 64.43 (64.15) | 6.71 (6.70) | 5.18 (5.13) | 148 |

-continued
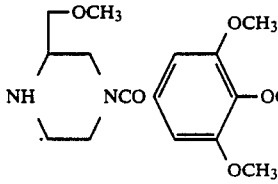
| Ex. No. | A | Molecular Formula | C | H | N | m.p. (°C.) |
|---|---|---|---|---|---|---|
| 9 | 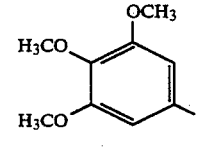 | $C_{26}H_{34}N_2O_9$ | 60.22 (59.78) | 6.61 (6.57) | 5.40 (5.23) | 157–158 |
| 10 | 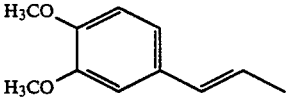 | $C_{25}H_{32}N_2O_8 \cdot \frac{1}{2}H_2O$ | 60.35 (60.33) | 6.69 (6.29) | 5.63 (5.69) | amorphous |
| 11 | 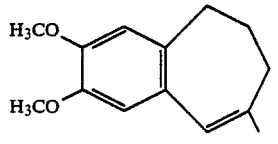 | $C_{27}H_{34}N_2O_8$ | 63.02 (62.83) | 6.66 (6.61) | 5.44 (5.50) | 134 |
| 12 | 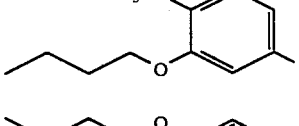 | $C_{30}H_{38}N_2O_8$ | 64.97 (64.58) | 6.91 (6.88) | 5.05 (4.68) | 137 |
| 13 | 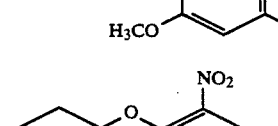 | $C_{28}H_{38}N_2O_8$ | 63.38 (63.45) | 7.21 (7.22) | 5.28 (5.09) | 74–76 |
| 14 | 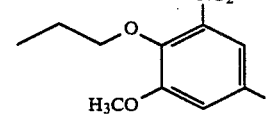 | $C_{28}H_{38}N_2O_8$ | 63.38 (63.09) | 7.21 (7.05) | 5.28 (5.21) | amorphous |
| 15 | 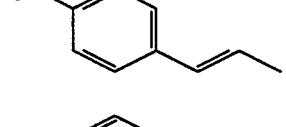 | $C_{27}H_{35}N_3O_{10}$ | 57.75 (57.70) | 6.28 (6.32) | 7.48 (7.55) | 144 |
| 16 | 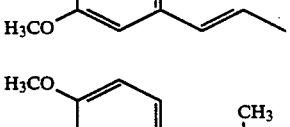 | $C_{26}H_{32}N_2O_7$ | 64.45 (64.40) | 6.65 (6.82) | 5.78 (5.50) | amorphous |
| 17 | 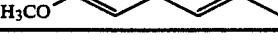 | $C_{26}H_{32}N_2O_7$ | 64.45 (64.51) | 6.65 (6.51) | 5.78 (5.26) | amorphous |
| 18 |  | $C_{28}H_{36}N_2O_8$ | 63.62 (63.42) | 6.86 (6.89) | 5.30 (5.13) | 146 |

WORKING EXAMPLE 19

A solution of 2,3-dimethoxy-6,7-dihydro-5H-benzocycloheptene-8-carbonyl chloride (0.36 g) in dichloromethane (6 ml) is added dropwise, at 0° C. while stirring, to a mixture of 3-methoxymethyl-1-(3,4,5trimethoxybenzyl)piperazine (0.4 g) obtained in Reference Example 14, triethylamine (0.3 g) and dichloromethane (6 ml). After stirring at room temperature for one hour, the reaction mixture is added to water, followed by extraction with dichloromethane. The organic layer is washed with water and dried, then the solvent is distilled off under reduced pressure. The residue is purified by means of a silica gel column chromatography (hexane:ethyl acetate:acetone=2:2:1) to afford 1-(2,3-dimethoxy-6,7-dihydro-5H-benzo-cyclohepten-8-ylcarbonyl) -2-methoxymethyl-4-(3,4,5-tri-methoxybenzyl)piperazine (0.6 g) as a colorless oily product. This product is converted to the hydrochloride, and treated with ethyl ether to give pale yellow powder.

Elemental Analysis for $C_{30}H_{40}N_2O_7 \times 4/5H_2O$:
Calcd.: C 60.91; H 7.26; N 4.74:
Found : C 60.92; H 6.98; N 4.75:

WORKING EXAMPLE 20

A solution of 2,3-dimethoxy-6,7-dihydro-5H-benzocycloheptene-8-carbonyl chloride (0.3 g) in dichloromethane (6 ml) is added dropwise, taking 3 minutes while stirring at 0° C., to a mixture of 3-ethoxymethyl-1-(3,4,5-trimethoxybenzoyl)piperazine (0.41 g) obtained in Reference Example 13, triethylamine (0.4 g) and dichloromethane (8 ml). After stirring for one hour at room temperature, the reaction mixture is added to water, followed by extraction with dichloromethane. The organic layer is washed with water and dried, then the solvent is distilled off under reduced pressure. The residue is purified by means of a silica gel chromatography (hexane:ethyl acetate:acetone=2:2:1) to afford 1(2,3-dimethoxy-6,7-dihydro-5H-benzocyclohepten-8-ylcarbonyl) -2-ethoxymethyl-4-(3,4 5trimethoxybenzoyl)piperazine (0.6 g) as a colorless oily product. This product is processed with ether to give colorless powder.

Elemental Analysis for $C_{31}H_{40}N_2O_8$:
Calcd.: C 65.48; H 7.09; N 4.93:
Found : C 65.18; H 7.25; N 4.64:

WORKING EXAMPLE 21

A solution of 2,3-dimethoxy-6,7-dihydro-5H-benzocycloheptene-8-carbonyl chloride (0.3 g) in dichloromethane (5 ml) is added dropwise, taking 3 minutes at 0° C with stirring, to a mixture of methyl 1-(3,4,5-trimethoxybenzoyl)piperazine-2-carboxylate (0.4 g), triethylamine (0.3 g) and dichloromethane (8 ml). The reaction mixture is stirred for thirty minutes at room temperature, nd then poured into water, followed by extraction with dichloromethane. The organic layer is washed with dilute hydrochloric acid, an aqueous solution of sodium hydrogencarbonate and water, successively, and then dried. The solvent is distilled off to afford methyl 4-(2,3-dimethoxy-6,7-dihydro-5H-benzocyclohepten-8-ylcarbonyl) -1-(3,4 5-trimethoxybenzoyl)-piperazine-2-carboxylate (0.63 g) as crystals. This product is recrystallized from ethanol and ethyl ether to give colorless crystals, m.p. 139-140° C.

Elemental Analysis for $C_{30}H_{36}N_2O_9$:
Calcd.: C 63.37; H 6.38; N 4.93:
Found : C 63.24; H 6.22; N 4.85:

WORKING EXAMPLE 22

A solution of 4-methoxy cinnamoyl chloride (0.3 g) in dichloromethane (4 ml) is added dropwise, taking 3 minutes at 0 ° C while stirring, to a mixture of methyl 1-(3,4,5-trimethoxybenzoyl)piperazine-2-carboxylate (0.57 g), triethylamine (0.4 g) and dichloromethane (12 ml). The reaction mixture is stirred for 30 minutes at room temperature, and then poured into water, followed by extraction with dichloromethane. The organic layer is washed with dilute hydrochloric acid, an aqueous solution of sodium hydrogencarbonate and water, successively, then the solvent is distilled off. The residue is purified by means of a silica gel column chromatography to give methyl 4-(4-methoxycinnamoyl)-1(3,4,5-trimethoxybenzoyl)piperazine-2-carboxylate (0.6 g) as a colorless oily product. This product is processed with ethyl ether to give colorless powder Elemental Analysis for $C_{26}H_{30}N_2O_8$:
Calcd.: C 62.64; H 6.07; N 5.62:
Found : C 62.39; H 6.12; N 5.59:

WORKING EXAMPLE 23

A mixture of methyl 1-(2,3-dimethoxy-6,7-dihydro-5H-benzocyclohepten-8-ylcarbonyl) piperazine-2carboxylate (1.2 g) obtained in Reference Example 18, 3,4,5-trimethoxybenzyl chloride (0.84 g), potassium carbonate (0.8 g) and acetonitrile (16 ml) is heated under reflux for 7 hours while stirring. The reaction mixture is poured into water, and extracted with ethyl acetate. The organic layer is washed with water and dried, then the solvent is distilled off under reduced pressure. The residue is purified by means of a silica gel column chromatography (hexane:ethyl acetate:acetone=3:3:1) to give methyl 1-(2,3-dimethoxy-6,7-dihydro-5H-benzocyclohepten-8-ylcarbonyl) -4-(3,4,5-trimethoxybenzyl)-piperazine-2-carboxylate as a pale yellow oily product (1.6 g). This product is then converted to its hydrochloride to become a white powdery product.

Elemental Analysis for $C_{30}H_{38}N_2O_8 \times HCl$:
Calcd.: C 60.96; H 6.65; N 4.74:
Found : C 60.82; H 6.92; N 4.53:

WORKING EXAMPLE 24

A mixture of 1-(2,3-dimethoxy-6 7-dihydro-5H-benzohepten-8-ylcarbonyl) -4-(3,4 5-trimethoxybenzyl)piperazine-2-carboxylate (0.9 g) obtained in Working Example 23, potassium carbonate (2.5 g), methanol (10 ml) and water (8 ml) is stirred for one hour at 70 ° C. The reaction mixture is concentrated under reduced pressure. The concentrate is processed with 10% hydrochloric solution to adjust its pH to 3-4. The reaction mixture is extracted with ethyl acetate. The organic layer is washed with water and dried, then the solvent is distilled off under reduced pressure to leave crystals of 1-(2,3-dimethoxy6,7-dihydro-5H-benzocyclohepten-8-ylcarbonyl) -4-(3 4 5-trimethoxybenzyl)piperazine-2-carboxylic acid (0.45 g). This product is recrystallized from ethyl acetate to give colorless crystals, m p.143-146° C.

Elemental Analysis for $C_{29}H_{36}N_2O_8 \times 3/2H_2O$:
Calcd.: C 61.36; H 6.93; N 4 94:
Found : C 61.33; H 6.72; N 4.98:

Then, to a mixture of 1-(2,3-dimethoxy-6,7-dihydro-5H-benzocyclohepten-8-ylcarbonyl) -4-(3,4,5trimethoxybenzyl)piperazine-2-carboxylic acid (0.4 g) obtained above, dimethylamine hydrochloride (0.3 g), triethylamine (0.85 g) and N,N-dimethylformamide (6 ml) is added dropwise, while stirring under ice-cooling, diethyl cyanophosphonate (0.6 g). The reaction mixture is stirred for 40 minutes at room temperature, and then poured into water, followed by extraction with ethyl acetate. The organic layer is washed with water and dried, then the solvent is distilled off under reduced pressure. The residue is purified by means of a silica gel column chromatography (hexane:ethyl acetate:acetone=1:1:1) to give crystals of N,N-dimethyl 1-(2,3-dimethoxy-6,7-dihydro-5H-benzocyclohepten-8-yl-carbonyl) -4-(3,4,5-trimethoxybenzyl)piperazine (0.37 g). This product is recrystallized from ethyl acetate to yield colorless needles, m.p.165–166° C.

Elemental Analysis for $C_{31}H_{41}N_3O_7$:
Calcd.: C 65.59; H 7.28; N 7.40:
Found : C 65.31; H 7.29; N 7.23:

WORKING EXAMPLE 25

A mixture of methyl 4-(2,3-dimethoxy-6,7-dihydro5H-benzocyclohepten-8-ylcarbonyl)piperazine-2carboxylate (2.0 g) obtained in Reference Example 15, 3,4,5-trimethoxybenzyl chloride (1.5 g), potassium carbonate (1.5 g) and acetonitrile (25 ml) is heated for 15 hours under reflux with stirring. The reaction mixture is concentrated under reduced pressure, and the concentrate is poured into water, followed by extraction with ethyl acetate. The organic layer is washed with water and dried, then the solvent is distilled off under reduced pressure. The residue is purified by means of a silica gel column chromatography (hexane:ethyl acetate:acetone=2:2:1) to afford methyl 4-(2,3-dimethoxy-6,7-dihydro-5H-benzocyclohepten-8-ylcarbonyl) -1-(3,4,5-trimethoxybenzyl)piperazine (2.6 g) as a colorless oily product. This product is then converted to its hydrochloride, which is processed with ethyl ether to give grayish white powder.

Elemental Analysis for $C_{30}H_{38}N_2O_8 \times HCl$:
Calcd.: C 60.96; H 6.65; N 4.74:
Found : C 60.71; H 6.85; N 4.48:

WORKING EXAMPLE 26

A mixture of methyl 4-(2,3-dimethoxy-6,7-dihydro5H-benzocyclohepten-8-ylcarbonyl) -1-(3,4,5-trimethoxybenzyl)piperazine-2-carboxylate (0.8 g) obtained in Working Example 25, potassium carbonate (3.0 g), methanol (10 ml) and water (8 ml) is stirred for 3 hours at 70 C. The reaction mixture is concentrated under reduced pressure. To the residue is added a solution of 10% hydrochloric acid to adjust the pH to 3-4, followed by extraction with ethyl acetate. The organic layer is washed with water and dried, then the solvent is distilled off under reduced pressure to leave crystals of 4-(2,3-dimethoxy-6,7-dihydro-5H-benzocyclohepten-8-ylcarbonyl) -1-(3,4,5-trimethoxybenzyl)piperazine-2-carboxylic acid (0.7 g). This product is recrystallized from ethyl acetate to give colorless crystals, m.p. 142–144° C.

Elemental Analysis for $C_{29}H_{36}N_2O_8 \times 1/2H_2O$:
Calcd.: C 63.37; H 6.79; N 5.10:
Found : C 63.34; H 6.72; N 5.05:

Then, to a mixture of 4-(2,3-dimethoxy-6,7-dihydro-5H-benzocyclohepten-8-ylcarbonyl) -1-(3 4 5-trimethoxybenzyl)piperazine-2-carboxylic acid (0.6 g) obtained above, dimethylamine hydrochloride (0.3 g), triethylamine (0.3 g) and N,N-dimethylforamide (8 ml) are added, under ice-cooling while stirring, diethyl cyanophosphonate (0.5 g) and triethylamine (0.3 g). After stirring for 2 hours at room temperature, the reaction mixture is poured into water, followed by extraction with ethyl acetate. The organic layer is washed with water and dried, then the solvent is distilled off under reduced pressure. The residue is purified by means of a silica gel column chromatography (hexane:ethyl acetate:acetone=1:1:1) to give N,N-dimethyl-4-(2,3-dimethoxy-6,7-dihydro-5H-benzocyclo-hepten-8-ylcarbonyl) -1-(3,4,5-trimethoxybenzyl)piperzine-2-carboxamide (0.6 g) as a pale yellow oily product. This product is led to its hydrochloride, followed by recrystallization from ethanol to yield colorless crystals, m.p. 173–176° C.

Elemental Analysis for $C_{31}H_{41}N_3O_7 \times HCl \times H_2O$:
Calcd.: C 59.85; H 7.13; N 6.75:
Found : C 59.99; H 6.87; N 6.68:

WORKING EXAMPLE 27-1

To a mixture of methyl 4-(2,3-dimethoxy-6,7-dihydro-5H-benzocyclohepten-8-ylcarbonyl) -1-(3,4,5-trimethoxybenzyl)piperazine-2-carboxylate (1.2 g) obtained in Working Example 25, sodium borohydride (0.45 g) and tetrahydrofuran (20 ml) is added methanol (3 ml) dropwise, taking one hour while heating under reflux. The reaction mixture is concentrated under reduced pressure To the residue is added water, followed by extraction with ethyl acetate. The organic layer is washed with water and dried, then the solvent is distilled off under reduced pressure. The organic layer is washed with water and dried, then the solvent is distilled off under reduced pressure. The residue is purified by means of a silica gel column chromatography (hexane:ethyl acetate:acetone=1:1:1) to afford 4-(2,3-dimethoxy-6,7-dihydro-5H-benzocyclohepten-8-ylcarbonyl) -1-(3,4,5-trimethoxybenzyl)piperazine-2-methanol as a colorless oily product (1.1 g). This product is led to its hydrochloride, which is then processed with ethyl ether to give a colorless powdery product.

Elemental Analysis for $C_{29}H_{38}N_2O_7 \times HCl \times 1/2H_2O$:
Calcd.: C 60.88; H 7.05; N 4.90:
Found : C 60.66; H 7.17; N 4.69:

WORKING EXAMPLE 27-2

A solution of 4-(2,3-dimethoxy-6,7-dihydro-5H-benzocyclohepten-8-ylcarbonyl) -1-(3,4,5-trimethoxybenzyl) piperazine-2-methanol (1.1 g) obtained in Working Example 27-1 in N,N-dimethylformamide (3 ml) is added dropwise, taking 3 minutes at 0° C. while stirring, to a mixture of sodium hydride (0.15 g) and N,N-dimethylformamide (4 ml). To the resulting mixture is then added methyl iodide (0.5 g) followed by stirring for one hour at room temperature. The reaction mixture is added to ice-water, and extracted with ethyl acetate. The organic layer is washed with water and dried, then the solvent is distilled off under reduced pressure. The residue is purified by means of a silica gel column chromatography (hexane:ethyl acetate:acetone=2:2:1) to give 1-(2,3-dimethoxy-6,7-dihydro-5H-benzocyclohepten-8-ylcarbonyl) -3-methoxymethyl-4-(3,4,5trimethoxybenzyl)piperazine (0.6 g) as a colorless oily product. This product is converted to its hydrochloride, which is processed with ether to cause precipitation to yield colorless powder.

Elemental Analysis for $C_{30}H_{40}N_2O_7 \times HCl \times 4/5H_2O$:
Calcd.: C 60.91; H 7.26; N 4.74:
Found : C 61.06; H 7.29; N 4.70:

WORKING EXAMPLE 28

To a mixture of ethyl 4-(2,3-dimethoxy-6,7-dihydro-5H-benzocyclohepten-8-ylcarbonyl) piperazine-2carboxylate (1.0 g) obtained in Reference Example 29, triethylamine (0.7 g) and dichloromethane (16 ml) is added dropwise, taking 3 minutes at 0° C. while stirring, a solution of 3,4,5-trimethoxybenzoyl chloride (0.65 g) in dichloromethane (12 ml). The reaction mixture is stirred for one hour at room temperature, and then poured into water, followed by extraction with dichloromethane. The organic layer is washed with dilute hydrochloric acid, an aqueous solution of sodium hydrogencarbonate and water, successively, and dried, then the solvent is distilled off under reduced pressure. The residue is purified by means of a silica gel column chromatography (hexane:ethyl acetate:acetone =2:2:1) to afford ethyl 4-(2,3-dimethoxy-6,7-dihydro-5H-benzocyclohepten-8-ylcarbonyl) -1-(3,4,5-trimethoxybenzoyl)piperazine-2carboxylate (1.4 g) as a colorless oily product. This product is processed with ethyl ether and hexane to cause precipitation to give colorless powder.

Elemental Analysis for $C_{31}H_{38}N_2O_9$:
Calcd.: C 63.90; H 6.57; N 4.81:
Found : C 63.62; H 6.59; N 4.67:

WORKING EXAMPLE 29

A mixture of ethyl 1-(2,3-dimethoxy-6,7-dihydro5H-benzocyclohepten-8-ylcarbonyl) -4-(3,4 5-trimethoxybenzoyl)piperazine-3-carboxylate (0.5 g) obtained in Working Example 28, potassium carbonate (1.0 g), methanol (10 ml) and water (10 ml) is stirred at 70 ° C for 20 minutes. The reaction mixture is concentrated under reduced pressure. To the mixture is added water, followed by acidifying with dilute hydrochloric acid. The mixture is subjected to extraction with ethyl acetate. The organic layer is washed with water and dried, then the solvent is distilled off under reduced pressure to leave crystals of 1-(2,3-dimethoxy-6,7-dihydro-5H-bonzocyclohepten-8-ylcarbonyl) -4-(3,4,5-trimethoxybenzoyl)piperazine-3carboxylic acid (0.38 g). This product is recrystallized from ethyl acetate to give colorless crystals, m.p. 198–199° C.

Elemental Analysis for $C_{29}H_{34}N_2O_9$:
Calcd.: C 62.81; H 6.18; N 5.05:
Found : C 62 81; H 6.25; N 5.00:

To a mixture of 4-(2,3-dimethoxy-6,7-dihydro-5H-benzocyclohepten-8-ylcarbonyl) -1-(3,4,5trimethoxybenzoyl)piperazine-2-carboxylic acid (0.45 g) obtained above, dimethylamine hydrochloride (0.37 g), triethylamine (0.7 g) and N,N-dimethylformamide (6 ml) are added, while stirring at 0° C., diethyl cyanophosphonate (0.6 g) and triethylamine (0.4 g). The reaction mixture is stirred at 0° C. for 30 minutes, and then poured into ice-water, followed by extraction with ethyl acetate The organic layer is washed with water and dried, then the solvent is distilled off under reduced pressure to leave N,N-dimethyl-4-(2,3-dimethoxy-6,7-dihydro-5H-benzocyclohepten-8-ylcarbonyl) -1-(3,4,5-trimethoxybenzoyl)piperazine-2-carboxamide as crystals (0.44 g). This product is recrystallized from ethyl acetate to give colorless needles, m.p. 177–178° C.

Elemental Analysis for $C_{31}H_{39}N_3O_8$:
Calcd.: C 64.01; H 6.76; N 7.22:
Found : C 63.89; H 6.74; N 7.04:

WORKING EXAMPLE 30-1

To a mixture of ethyl 4-(2,3-dimethoxy-6,7-dihydro-5H-benzocyclohepten-8-ylcarbonyl) -1-(3,4,5-trimethoxybenzoyl)piperazine-2-carboxylate (0.5 g) obtained in Working Example 28, sodium borohydride (0.4 g) and tetrahydrofuran (15 ml) is added dropwise, while heating under reflux, methanol (3 ml) taking 40 minutes. The reaction mixture is concentrated under reduced pressure, and the concentrate is subjected to extraction with ethyl acetate. The organic layer is washed with water and dried, then the solvent is distilled off under reduced pressure. The residue is purified by means of a silica gel column chromatography (hexane:ethyl acetate:acetone=1:1:1) to give 4-(2,3-dimethoxy-6,7-dihydro-5H-benzocyclohepten-8-yl-carbonyl) -1-(3,4,5-trimethoxybenzoyl)piperazine methanol (0.45 g) as a colorless oily product. This product is processed with ethyl ether to give colorless powder.

Elemental Analysis for $C_{29}H_{36}N_2O_8$:
Calcd.: C 64.43; H 6.71; N 5.19:
Found : C 64.18; H 6.86; N 5.02:

WORKING EXAMPLE 30-2

To a mixture of sodium hydride (0.07 g) and N,N-dimethylformamide (5 ml) is added, while stirring at 0° C., 4-(2,3-dimethoxy-6,7-dihydro-5H-benzocyclohepten-8-ylcarbonyl) -1-(3,4,5-trimethoxybenzoyl)piperazine-2-methanol (0.35 g) obtained in Working Example 30-1. To the mixture is then added methyl iodide (0.2 g), followed by stirring at 0° C. for 30 minutes. The reaction mixture is poured into ice-water and extracted with ethyl acetate. The organic layer is washed with dilute hydrochloric acid, an aqueous solution of sodium hydrogencarbonate and water, successively and dried, then the solvent is distilled off under reduced pressure. The residue is purified by means of a silica gel column chromatography (hexane:ethyl acetate:acetone=1:1:1) to give 1-(2,3-dimethoxy-6,7-dihydro-5H-benzocyclohepten-8-ylcarbonyl) -3-methoxymethyl-4(3,4,5-trimethoxybenzoyl)piperazine (0.25 g) as a colorless oily product. This product is triturated with ether to give colorless powder.

Elemental Analysis for $C_{30}H_{38}N_2O_8$:
Calcd.: C 64.97; H 6.91; N 5.05:
Found : C 64.80; H 7.13; N 4.79:

WORKING EXAMPLE 31

A solution of 2,3-dimethoxy-6,7-dihydro-5H-benzocycloheptene-8-carbonyl chloride (0.53 g) in dichloromethane (8 ml) is added dropwise, while stirring at 0° C. for 3 minutes, to a mixture of ethyl 4-(3,4,5-trimethoxybenzoyl)piperazine-2-carboxylate (0.7 g), triethylamine (0.5 g) and dichloromethane (15 ml). The reaction mixture is stirred for 2 hours at room temperature, and then poured into ice-water, followed by extraction with dichloromethane. The organic layer is washed with dilute hydrochloric acid, an aqueous solution of sodium hydrogencarbonate and water, successively, and dried, then the solvent is distilled off under reduced pressure. Crystals obtained from the residue are recrystallized from ethyl acetate and hexane to give ethyl 1-(2,3-dimethoxy-6,7-dihydro-5H-benzocyclohepten-8-ylcarbonyl) -4-(3,4,5-trimethoxybenzoyl)piperazine-2-carboxylate as colorless crystals (0.9 g), m.p. 108–110° C.

Elemental Analysis for $C_{31}H_{38}N_2O_9$:
Calcd.: C 63.90; H 6.57; N 4.81:

Found : C 63.68; H 6.63; N 4.87:

WORKING EXAMPLE 32-1

Ethyl 1-(2,3-dimethoxy-6,7-dihydro-5H-benzocyclohepten-8-ylcarbonyl) -4-(3,4,5-trimethoxybenzoyl)-piperazine-2-carboxylate obtained in Working Example 31 is subjected to reduction with sodium borohydride and methanol in tetrahydrofuran in the same manner as with Working Example 27-1 to give 1-(2,3-dimethoxy-6,7-dihydro-5H-benzocyclohepten-8-ylcarbonyl) -4- (3,4,5-trimethoxybenzoyl)piperazine. This product is recrystallized from ethyl acetate to afford colorless crystals, m.p. 169° C.

Elemental Analysis for $C_{29}H_{36}N_{O8}$:
Calcd.: C 64.43; H 6.71; N 5.18:
Found : C 64.18; H 6.66; N 5.09:

WORKING EXAMPLE 32-2

Sodium hydride (30 mg) is added to a mixture of 1(2,3-dimethoxy-6,7-dihydro-5H-benzocyclohepten-8-ylcarbonyl) -4-(3,4,5-trimethoxybenzoyl)piperazine-methanol (290 mg) and tetrahydrofuran (5 ml) at 0° C. The mixture is stirred for 2 hours. To the resultant mixture is added methyl iodide (130 mg) at room temperature, followed by stirring for further 3 hours. The reaction mixture is poured into ice-water, followed by extraction with dichloromethane. The extract solution is washed with an aqueous solution of citric acid, which is dried and then concentrated. The concentrate is subjected to a silica gel column chromatography (eluent:ethyl acetate-hexane=4:1:1) to afford 1-(2,3-dimethoxy-6,7-dihydro-5H-benzocyclohepten-8-ylcarbonyl) -2-methoxymethyl-4-(3,4,5-trimethoxybenzoyl)piperazine (250 mg) as colorless crystals, m.p. 137° C.

Elemental Analysis for $C_{30}H_{38}N_2O_8$:
Calcd.: C 64.97; H 6.91; N 5.05:
Found : C 63.58; H 6.88; N 4.68:

WORKING EXAMPLE 33

In dichloromethane (18 ml) is dissolved 2,3-dimethoxy-6,7-dihydro-5H-benzocycloheptene-8-carbonyl chloride (1.44 g). The solution is added dropwise taking 5 minutes, while stirring at 0° C., to a mixture of methyl 1-(3,4,5-trimethoxybenzyl)piperazine-2carboxylate dihydrochloride (2.16 g), triethylamine (2.5 g) and dichloromethane (25 ml). The reaction mixture is stirred for one hour at room temperature, and then poured into ice-water, followed by extraction with dichloromethane. The organic layer is washed with water and dried, then the solvent is distilled off under reduced pressure. The residue is purified by means of a silica gel column chromatography (hexane:ethyl acetate:acetone =3:3:1) to afford methyl 4-(2 3-dimethoxy-6,7-dihydro-5H-benzocyclohepten-8-ylcarbonyl) -1-(3,4,5-trimethoxybenzyl)piperazine -2- carboxylate, which is identical with the product obtained in Working Example 25, as a colorless oily product (2.2 g).

WORKING EXAMPLE 34

In dichloromethane (15 ml) is dissolved 2 3-dimethoxy-6,7-dihydro-5H-benzocycloheptene-8-carboxylic acid chloride (1.2 g). The solution is added dropwise taking 5 minutes, while stirring at 0° C., to a mixture of methyl 4-(3,4,5-trimethoxybenzyl)piperazine-2carboxylate dihydrochloride (1.8 g) obtained in Reference Example 27, triethylamine (2.0 g) and dichloromethane (20 ml). The reaction mixture is stirred at room temperature for 2 hours, and then poured into ice-water, followed by extraction with dichloromethane. The organic layer is washed with water and dried, then the solvent is distilled off. The residue is purified by means of a silica gel column chromatography (hexane:ethyl acetate:acetone=2:2:1)to afford methyl 1-(2,3-dimethoxy-6,7-dihydro-5H-benzocyclohepten-8-ylcarbonyl) -4-(3,4,5-trimethoxybenzyl)piperazine-2-carboxylate, which is identical with the compound obtained in Working Example 23, as a pale yellow oily product (1.8 g).

WORKING EXAMPLE 35

A mixture of 1-(2,3-dimethoxy-6,7-dihydro-5H-benzocyclohepten-8-ylcarbonyl) -4-(3,4,5-trimethoxybenzyl)piperazine-2-methanol (500 mg) obtained by the method in Working Example 19 and N,N-dimethylformamide (3 ml) is cooled to 0° C., to which is added, in limited amounts, 60% oily sodium hydride (80 mg). The reaction mixture is stirred for 30 minutes and then cooled to −20° C., followed by adding thereto dropwise a mixture of ethyl iodide (200 mg) and N,N-dimethylformamide (1 ml). After stirring for 4 hours at −20° C., the reaction mixture is poured into ice-water, followed by extraction with methylene chloride. The organic layer is washed with water, dried over anhydrous magnesium sulfate and concentrated under reduced pressure. The concentrate is purified by means of a silica gel column chromatography (eluent:ethyl acetate-hexane-methanol=50:45:5) to give 1-(2,3-dimethoxy-6,7-dihydro-5H-benzocyclohepten-8-ylcarbonyl) -2-ethoxymethyl-4-(3,4,5trimethoxybenzyl)piperazine as a colorless oily product (420 mg). This product is dissolved in ethyl acetate and converted to its hydrochloride with 4N HCl (ethyl acetate solution). To the mixture is added ethyl ether, and left standing to give the hydrochloride as colorless crystals, m.p. 169–171° C.

Elemental Analysis for $C_{31}H_{42}N_2O_7 \times HCl \times 1/2H_2O$:
Calcd.: C 62.04; H, 7.39; N, 4.67:
Found : C 62.45; H, 7.32; N, 4.75:

WORKING EXAMPLES 36-39

By the manner of Working Example 35, 1-(2,3-dimethoxy-6,7-dihydro-5H-benzocyclohepten-8-ylcarbonyl) -4-(3,4,5-trimethoxybenzyl)piperazine-2-methanol is allowed to react with an organic halogenide to give the compounds of Working Examples 36-39.

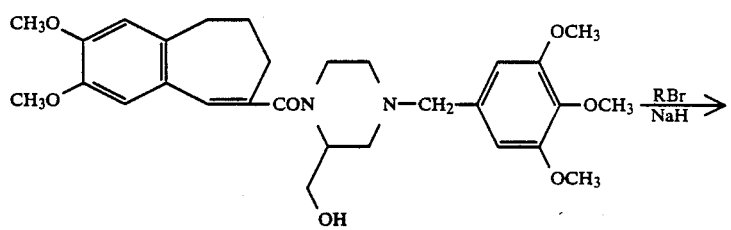

-continued

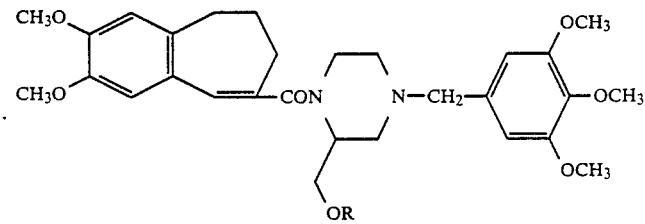

| W.E. No. | R | Molecular Formula | Elemental Analysis Calcd. (Found) | | | m.p. (°C.) |
|---|---|---|---|---|---|---|
| | | | C | H | N | |
| 36 | CH₃CH₂CH₂— | C₃₂H₄₄N₂O₇·HCl·½H₂O | 62.58 (62.29) | 7.55 (7.71) | 4.56 (4.48) | 152–156 |
| 37 | H₂C=CHCH₂— | C₃₂H₄₂N₂O₇·HCl | 63.72 (63.70) | 7.19 (7.39) | 4.64 (4.63) | 154–157 |
| 38 | HC≡C—CH₂— | C₃₂H₄₀N₂O₇·HCl | 63.94 (63.84) | 6.87 (6.87) | 4.66 (4.73) | white powder |
| 39 | ▷—CH₂— | C₃₃H₄₄N₂O₇·HCl | 64.22 (64.10) | 7.35 (7.60) | 4.54 (4.58) | white powder |

WORKING EXAMPLE 40

A mixture of 1-(2,3-dimethoxy-6,7-dihydro-5H-benzocyclohepten-8-ylcarbonyl) -4-(3,4,5-trimethoxybenzyl)piperazine-2-methanol (500 mg), acetic anhydride (153 mg), triethylamine (150 mg), 4-dimethylaminopyridine (10 mg) and methylene chloride (5 ml) is stirred for 20 hours at room temperature. To the reaction mixture is added methylene chloride, and the organic layer is washed with an aqueous solution of sodium hydrogencarbonate, dried over anhydrous magnesium sulfate, then concentrated under reduced pressure. The concentrate is purified by means of a silica gel column chromatography (eluent:ethyl acetate) to give 2-acetoxymethyl-1-(2,3-dimethoxy-6,7-dihydro-5H-benzocyclohepten-8-ylcarbonyl) -4-(3,4,5-trimethoxybenzyl)piperazine (420 mg). This product is converted to its hydrochloride, followed by recrystallization from ethanol to give colorless prisms, m.p. 135–139° C.

Elemental Analysis for C₃₁H₄₀N₂O₈×HCl×1/2-H₂O:
Calcd.: C 60.63; H, 6.89; N, 4.56:
Found : C 60.53; H, 7.03; N, 4.38:

WORKING EXAMPLE 41

A mixture of 1-(2,3-dimethoxy-6 7-dihydro-5H-benzocyclohepten-8-ylcarbonyl) -4-(3,4,5-trimethoxybenzyl)piperazine-2-methanol (500 mg), methyl isocyanate (100 mg), triethylamine (200 mg) and methylene chloride (5 ml) is stirred for 5 hours at room temperature. To the reaction mixture is added methylene chloride, and the organic layer is washed with an aqueous solution of sodium hydrogencarbonate, dried over anhydrous magnesium sulfate and concentrated under reduced pressure. The concentrate is purified by means of a silica gel column chromatography (eluent:ethyl acetate-hexane-methanol=5:4:1) to give 1(2,3-dimethoxy-6,7-dihydro-5H-benzocyclohepten-8-ylcarbonyl) -2-N-methylcarbamoyloxymethyl-4-(3,4,5-trimethoxybenzyl)piperazine (440 mg). This product is converted to its hydrochloride, followed by recrystallization from ethanol to give colorless crystals, m.p. 161–163° C.

Elemental Analysis for C₃₁N₄₁O₈×HCl:
Calcd.: C 60.04; H, 6.83; N, 6.78:
Found : C 60.01; H, 6.98; N, 6.49:

WORKING EXAMPLE 42

To a solution of oxalyl chloride (175 mg) in methylene chloride (1 ml) is added dropwise at −78° C. a solution of dimethyl sulfoxide (215 mg) in methylene chloride (1 ml), and the mixture is stirred for 10 minutes. To the reaction mixture is added a solution of 1-(2,3-dimethoxy-6,7-dihydro-5H-benzocyclohepten-8-ylcarbonyl) -4-(3,4,5-trimethoxybenzyl)piperazine-2-methanol (500 mg) in methylene chloride (2 ml), and the mixture is stirred for 10 minutes. To the reaction mixture is added triethylamine (650 mg), then the reaction temperature is raised up to room temperature. To the reaction mixture is then added water, followed by extraction with methylene chloride. The organic layer is washed with water, dried and concentrated under reduced pressure. The concentrate is dissolved in methanol (5 ml). To the mixture are added dimethylamine hydrochloride (200 mg) and sodium cyanoborohydride (130 mg). The reaction mixture is stirred for 48 hours at room temperature and then poured into a 1N NaOH solution, followed by extraction with methylene chloride. The organic layer is washed with water, dried and concentrated under reduced pressure. The concentrate is purified by means of a silica gel column chromatography (eluent:methanol ethyl acetate=15:85) to give 1-(2,3-dimethoxy-6,7-dihydro-5H-benzocyclohepten-8-ylcarbonyl) -2-dimethylaminomethyl-4-(3,4,5-trimethoxybenzyl) piperazine (200 mg). This product is converted to its hydrochloride, followed by recrystallization from ethanol to give colorless prisms, m.p. 167–169° C.

Elemental Analysis for C₃₁N₃O₆×2HCl:
Calcd.: C 59.42; H, 7.24; N, 6.71:
Found : C 59.18; H, 7.33; N, 6.68:

WORKING EXAMPLE 43

To a solution of oxalyl chloride (360 mg) in methylene chloride (5 ml) is added dropwise at −78° C. a (340 mg) solution of dimethyl sulfoxide (340 mg) in methylene chloride (2 ml), and the mixture is stirred for 10 minutes. To the resulting reaction mixture is added dropwise a solution of 1-(2,3-dimethoxy-6,7-dihydro-5H-benzocyclohepten-8-ylcarbonyl) -4-(3,4,5-trimethoxybenzyl)piperazine-2-methanol (750 mg) in methylene chloride (2 ml), then the mixture is stirred for 15 minutes. To the reaction mixture is added triethylamine (1 g), then the reaction temperature is raised up to room temperature. The reaction mixture is poured into ice-water, followed by extraction with methylene chloride. The organic layer is washed with water, dried and concentrated under reduced pressure. The concentrate is dissolved in methanol (10 ml). To the solution is added diethylamine hydrochloride (1.4 g), and the mixture is stirred for 3 hours at 50° C. To the reaction mixture is added, after cooling, sodium cyanoborohydride (90 mg), followed by stirring for one hour at room temperature. The reaction mixture is poured into ice-water, followed by extraction with methylene chloride. The organic layer is washed with water, dried and concentrated under reduced pressure. The concentrate is purified by means of a silica gel column chromatography (eluent:ethyl acetate-methanol=9:1) to give 2-diethylaminomethyl-1-(2,3-dimethoxy-6,7-dihydro-5H-benzocyclohepten-8-ylcarbonyl) -4-(3,4,5-trimethoxybenzyl)piperazine (230 mg). This product is converted to its hydrochloride, followed by recrystallization from ethanol to give colorless crystals, m.p. 157–160° C.

Elemental Analysis for $C_{33}H_{47}N_3O_6 \times 2HCl$:
Calcd.: C 60.54; H, 7.54; N, 6.42:
Found : C 60.47; H, 7.60; N, 6.40:

WORKING EXAMPLE 44

A mixture of 1-(2,3-dimethoxy-6,7-dihydro-5H-benzocyclohepten-8-ylcarbonyl) -4-(3,4,5-trimethoxybenzyl)piperazine-2-methanol (500 mg), dimethyl disulfide (940 mg), tri-n-butyl phosphine (2.0 g) and N,N-dimethylformamide (5 ml) is stirred at room temperature for 20 hours. The reaction mixture is poured into dilute hydrochloric acid, followed by washing with ethyl ether. The aqueous layer is made basic with sodium hydrogencarbonate, extracted with methylene chloride. The organic layer is washed with water, dried and concentrated under reduced pressure. The concentrate is purified by means of a silica gel column chromatography (eluent: ethyl acetate) to give 1-(2,3-dimethoxy-6,7-dihydro-5H-benzocyclohepten-8-yl-carbonyl -2-methylthiomethyl-4-(3,4,5-trimethoxybenzyl)piperazine (40 mg). This product is converted to its hydrochloride to give colorless powder.

Elemental Analysis for $C_{30}H_{40}N_2O_6S \times HCl \times 2H_2O$:
Calcd.: C 57.27; H, 7.21; N, 4.45:
Found : C 57.50; H, 7.05; N, 4.42:

WORKING EXAMPLE 45

To a mixture of 4-(3,4,5-trimethoxybenzyl)-2-piperazine propanol (1.0 g) obtained in Reference Example 32, triethylamine (1.5 g) and methylene chloride (20 ml) is added dropwise at 0 ° C, while stirring, a solution of 2,3-dimethoxy-6,7-dihydro-5H-benzocycloheptene-8-carbonyl chloride (713 mg) in methylene chloride (5 ml). The mixture is stirred for 2 hours and there is added an aqueous solution of sodium hydrogencarbonate, followed by shaking. The organic layer is separated, washed with water, dried and concentrated under reduced pressure. The concentrate is purified by means of a silica gel column chromatography (eluent:ethyl acetate-hexane methanol=5:4:1), followed by recrystallization from ethyl acetate to give 1-(2,3-dimethoxy-6,7-dihydro-5H-benzocyclohepten-8-ylcarbonyl) -4-(3,4,5-trimethoxybenzyl)-2-piperazine propanol as colorless prisms (1.05 g), m.p. 144–145° C.

Elemental Analysis for $C_{31}H_{42}N_2O_7$:
Calcd.: C 67.13; H, 7.63; N, 5.05:
Found : C 66.76; H, 7.74; N, 4.98:

WORKING EXAMPLE 46

To a solution of 1-(2,3-dimethoxy-6,7-dihydro-5H-benzocyclohepten-8-ylcarbonyl) -4-(3,4,5-trimethoxybenzyl)-2-piperazine propanol (500 mg) obtained in Working Example 45, in pyridine (2 ml) is added at −20° C. p-toluene sulfonyl chloride (190 mg), and the mixture is stirred for 10 minutes. The reaction mixture is poured into an aqueous solution of sodium hydrogencarbonate, followed by extraction with methylene chloride. The organic layer is washed with water, dried and concentrated under reduced pressure. The concentrate is dissolved in dimethyl sulfoxide (5 ml). To the solution is added sodium borohydride (340 mg), and the mixture is stirred for one hour at 80° C.

After cooling the reaction mixture is poured into an aqueous solution of sodium hydrogencarbonate, followed by extraction with ethyl acetate. The organic layer is washed with water, dried and concentrated under reduced pressure. The concentrate is purified by means of a silica gel column chromatography (eluent: ethyl acetate-hexane-methanol=5:4:1), and the product is converted to its hydrochloride, followed by recrystallization from ethanol to give 1-(2,3-dimethoxy-6,7-dihydro-5H-benzocyclohepten-8-ylcarbonyl) 2-propyl-4-(3,4,5-trimethoxybenzyl)piperazine hydrochloride as colorless prisms (220 mg), m.p. 172–176° C.

Elemental Analysis for $C_{31}H_{42}N_2O_6 \times HCl$:
Calcd.: C 64.74; H, 7.54; N, 4.87:
Found : C 64.50; H, 7.44; N, 4.80:

WORKING EXAMPLE 47

To a mixture of 3-methoxyethyl-1-(3,4,5-trimethoxybenzyl)piperazine dihydrochloride (500 mg) obtained in Reference Example 14, imidazo[1,2-a]pyridine-2-carboxylic acid (211 mg), triethylamine (657 mg) and N,N-dimethylformamide (3 ml) is added dropwise under ice-cooling, while stirring, a solution of diethyl cyanophosphonate (277 mg) in N,N-dimethylformamide (1 ml), and the mixture is stirred for one hour. The reaction mixture is poured into ice-water and extracted with ethyl acetate. The organic layer is washed with water, dried and concentrated under reduced pressure. The concentrate is purified by means of a silica gel column chromatography (eluent:ethyl acetate), followed by recrystallization to give 2-[2-methoxymethyl-4-(3,4,5-trimethoxybenzyl)piperazin-l-ylcarbonyl]imidazo[1,2-a]-pyridine as colorless prisms (354 mg), m.p. 129–130° C.

Elemental Analysis for $C_{24}H_{30}N_4O_5$:
Calcd.: C 63.42; H, 6.65; N, 12.23:
Found : C 63.27; H, 6.65; N, 12.43:

WORKING EXAMPLES 48-51

In substantially the same manner as described in Example 47, 3-methoxymethyl-1-(3,4,5trimethoxybenzyl)-piperazine dihydrochloride and carboxylic acid are subjected to condensation, in the presence of triethylamine, by using diethyl cyanophosphonate in N,N- dimethylformamide (DMF) to give compounds of Working Examples 48–51.

stirred at 0° C. for one hour and there poured into ice-water, followed by extraction with ethyl acetate. The

| W.E. No. | A | Molecular Formula | Elemental Analysis Calcd. (Found) | | | m.p. (°C.) |
|---|---|---|---|---|---|---|
| | | | C | H | N | |
| 48 | (2-pyridyl with CH=CH-N) | $C_{24}H_{30}N_4O_5 \cdot 2HCl \cdot \frac{1}{2}H_2O$ | 53.73 (53.31) | 6.20 (6.41) | 10.44 (10.55) | 165–166 |
| 49 | (pyrazinyl-thiazolyl) | $C_{25}H_{30}N_4O_5S$ | 60.22 (60.09) | 6.06 (6.07) | 11.24 (11.43) | 108 |
| 50 | (3,4-dimethoxyphenyl-thiazolyl) | $C_{28}H_{35}N_3O_7S$ | 60.31 (60.29) | 6.33 (6.32) | 7.53 (7.50) | 154 |
| 51 | (3,4-difluorophenyl-thiazolyl) | $C_{28}H_{29}N_3O_5SF_2$ | 58.53 (58.33) | 5.48 (5.50) | 7.88 (7.91) | 136–137 |

WORKING EXAMPLE 52

To a mixture of 2-methoxymethyl-4-(3,4,5trimethoxybenzoyl)piperazine hydrochloride obtained in Reference Example 6 (0.52 g), 2-(3-pyridyl)thiazol-4-carboxylic acid (0.3 g), triethylamine (0.46 g) and N,N-dimethylformamide (3 ml) is added dropwise, while stirring under icecooling, diethyl cyanophosphonate (0.47 g). The reaction mixture is stirred at 0° C. for one hour, and then poured into ice-water, followed by extraction with ethyl acetate. The organic layer is washed with water, dried and concentrated under reduced pressure. The concentrate is purified by means of a silica gel column chromatography (eluent:AcOEt-CH$_2$Cl$_2$—CH$_3$OH=10:9:1) to give 2-methoxymethyl-1-[2-(3-pyridyl)thiazol-4-ylcarbonyl]-4-(3,4,5-trimethoxybenzoyl) piperazine. Recrystallization from ethanol gives colorless needles m.p. 149–150° C.

Elemental analysis for $C_{25}H_{28}N_4O_6S \times 1/3H_2O$:
Calcd.: C 57.90; H, 5.57; N, 10.80:
Found : C 58.12; H, 5.52; N, 10 86:

WORKING EXAMPLES 53

To a mixture of 2-methoxymethyl-4-(3,4,5trimethoxybenzoyl) piperazine hydrochloride obtained in Reference Example 6 (0.50 g), 2-(3,4-dimethoxyphenyl)thiazol-4-carboxylic acid (0.37 g), triethylamine (0.42 g) and N,N-dimethylformamide (5 ml) is added dropwise, while stirring under icecooling, diethyl cyanophosphonate (0.46 g). The reaction mixture is organic layer is washed with water, dried and concentrated under reduced pressure. The concentrate is purified by means of a silica gel column chromatography (eluent: AcOEt) to give 1-[2-(3,4-dimethoxyphenyl) thiazol-4-ylcarbonyl]-2-methoxymethyl-4-(3,4,5-trimethoxybenzoyl)piperazine. Recrystallization from EtOH gives colorless needles, m.p. 149–151° C.

Elemental analysis for $C_{28}H_{33}N_3O_8S \times 1/2H_2O$
Calcd.: C, 57.92; H, 5.90; N, 7.24:
Found : C, 58.22; H, 5.81; N, 7.36:

WORKING EXAMPLE 54

To a solution of ethyl 1-(2,3-dimethoxy-6,7-dihydro-5H-benzocyclohepten-8-ylcarbonyl) -4-(3,4,5-trimethoxybenzoyl)piperazine-2-carboxylate (1.2 g) in methanol (15 ml) are added potassium carbonate (3.0 g) and water (8 ml) and the mixture is stirred at 70° C. for 30 minutes. To the reaction mixture is added water (50 ml). The mixture is washed with ethyl acetate. The aqueous layer is made acid with dilute hydrochloric acid, followed by extraction with ethyl acetate. The organic layer is washed with water, dried and concentrated under reduced pressure to give a crude product of 1-(2,3-dimethoxy-6,7-dihydro-5H-benzocyclohepten-8-ylcarbonyl) -4-(3,4,5-trimethoxybenzoyl)piperazine-2-carboxylic acid (1.1 g) as a colorless oily substance. To a mixture of this crude product (0.75 g), triethylamine (0.14 g) and N,N-dimethylformamide (4 ml) is added dropwise, while stirring under ice-cooling, diphenylphosphoryl azide (0.37 g). The reaction mixture is poured into ice-water, followed by extraction with benzene. The organic layer is washed with water and dried, followed by distilling off the solvent under reduced pressure until the whole volume becomes about 20 ml. The resultant solution is heated under reflux for 30 minutes. To the mixture is added methanol (5 ml), followed by heating under reflux for further one hour. The reaction mixture is concentrated under reduced pressure, and the concentrate is purified by means of a silica gel column chromatography (eluent hexane ethyl acetate-acetone=1:1:1) to give crystals, which are recrystallized from ethyl acetate to give 1-(2,3-dimethoxy-6,7-dihydro-5H-benzocyclohepten-8-ylcarbonyl)-2-methoxycarbonylamino-4-(3,4,5-trimethoxybenzoyl)piperazine as colorless crystals (0.6 g), m.p. 143-145° C.

Elemental Analysis for $C_{30}H_{37}N_3O_9$:
Calcd.: C 61.74; H, 6.39; N, 7.20:
Found : C 61.62; H, 6.12; N, 7.05:

The compounds (I) of the present invention and their salts are excellent in absorption from the intestinal canal and show excellent PAF antagonism even by oral administration. Therefore, the compounds (I) and their salts can be administered not only non-orally such as by injection, but also orally.

The following test examples explain the effects of the present invention in a more concrete manner.

TEST EXAMPLE 1

Inhibitory action on PAF-induced platelet aggregation

Blood was collected from the hearts of conscious New Zealand white male rabbits weighing 2 to 3 Kg using citric acid as an anticoagulant (one volume part of 3.15% citric acid relative to 9 volume parts of the whole blood). The blood was subjected to a centrifuge at 800 rpm for 10 minutes to obtain platelet rich plasma (PRP). The remaining blood after collecting the PRP was subjected to a centrifuge at 3000 rpm for 10 minutes to obtain platelet poor plasma (PPP). PRP was diluted with PPP to adjust the number of platelets to about 500,000/μl. Platelet aggregation was examined by means of turbidimetry [Born, Nature, 194, 927-929(1962)]with 8 channel aggregometer (NBS HEMA TRACER 6 Nikoh, Bio-science, Japan). More concretely, PRP(250 μl) was kept warm (37° C.) for 3 minutes in a silicon-processed cuvette, to which was added a test sample (25 μl) prepared by dissolving a compound of this invention in a physiological saline or a test sample (25 μl) prepared by dissolving a compound of this invention in 10 mM dimethylsulfoxide and diluting with a physiological saline. Two minutes later, PAF (25 μl), $3\times10^{-9}$ to $1\times10^{-8}$M) dissolved in a physiological saline was added and then the maximum aggregation rate was determined. As the control, physiological saline without test sample was used, and the inhibitory rate thereon was determined.

TABLE 1

| No. of Working Example corresponding to test compound | Platelet Aggregation Inhibitory Action(%) Concentration of test compound | |
|---|---|---|
| | $3 \times 10^{-8}$ M | $3 \times 10^{-5}$ M |
| 1 | 61 | 100 |
| 2 | | 89 |
| 3 | | 76 |

TABLE 1-continued

| No. of Working Example corresponding to test compound | Platelet Aggregation Inhibitory Action(%) Concentration of test compound | |
|---|---|---|
| | $3 \times 10^{-8}$ M | $3 \times 10^{-5}$ M |
| 7 | 100 | 100 |
| 8 | 75 | 100 |
| 12 | 100 | 100 |
| 19 | 100 | 100 |
| 20 | 100 | |
| 21 | 60 | 100 |
| 23 | 84 | 100 |
| 27-2 | 43 | 100 |
| 30-2 | 80 | 100 |
| 35 | 100 | 100 |
| 36 | 88 | 100 |
| 37 | 100 | 100 |
| 38 | 100 | 100 |
| 39 | 75 | 100 |
| 40 | 67 | 100 |
| 41 | 54 | 100 |
| 42 | 88 | 100 |
| 43 | 100 | 100 |
| 44 | | 100 |
| 46 | 47 | 100 |
| 47 | | 100 |
| 48 | | 100 |
| 49 | 55 | 100 |
| 50 | 100 | 100 |
| 51 | 63 | 100 |
| 52 | 31 | 100 |
| 53 | 100 | 100 |
| 54 | 26 | 100 |

TEST EXAMPLE 2

Inhibitory action on PAF-induced hypotension

SD(Jcl) male rats 6 to 8 week old were applied with cannulation into the femoral artery and vein under anesthesia with pentabarbital. The animals were fasted overnight, then subjected to the experiment. A transducer (MPU-0.5-290-0-III, TOYO BALDWIN, Japan) was connected with the artery cannula, and blood pressure was continuously measured by means of polygraph (Sanei, Japan). When the blood pressure became constant, PAF(0.5 to 1.0 μg/kg) dissolved in a physiological saline was injected through the venous cannula to lower the blood pressure by 30 to 45 mmHg. Thirty minutes later, PAF was injected again, and the average of lowered values of blood pressure (twice) was used as the control. After restoration of blood pressure to the initial level, test samples prepared by dissolving or suspending the drug in a physiological saline suspension of gum arabic (5%) were orally administered (5 ml/kg), then, after 1, 2 and 4 hours, PAF was injected. The rate of inhibition of lowering of blood pressure after administration of the test samples against the control was evaluated.

The results are shown in Table 2.

TABLE 2

| No. of Working Example corresponding to test compound | Dosage (mg/kg) | Inhibitory Action on PAF-Induced Hypotension (%) | | |
|---|---|---|---|---|
| | | After 1 hr. | After 2 hr. | After 4 hr. |
| 1 | 30 | 51 | 87 | 95 |
| 7 | 30 | 100 | 100 | 100 |
| 8 | 30 | 92 | 100 | 100 |
| 12 | 30 | 100 | 100 | 100 |
| 12 | 3 | 69 | 55 | 39 |
| 19 | 3 | 78 | 58 | 38 |
| 20 | 3 | 81 | 71 | 56 |
| 21 | 30 | 87 | 94 | 100 |

TABLE 2-continued

| No. of Working Example corresponding to test compound | Dosage (mg/kg) | Inhibitory Action on PAF-Induced Hypotension (%) | | |
|---|---|---|---|---|
| | | After 1 hr. | After 2 hr. | After 4 hr. |
| 23 | 30 | 94 | 94 | 90 |
| 27-2 | 30 | 100 | 100 | 100 |
| 30-2* | 100 | 100 | 100 | 100 |
| 35 | 30 | 100 | 100 | 79 |
| 36 | 30 | 100 | 100 | 100 |
| 37 | 30 | 100 | 100 | 57 |
| 40 | 30 | 100 | 100 | 24 |
| 41 | 30 | 100 | 50 | 16 |
| 42 | 30 | 100 | 100 | 91 |
| 49 | 30 | 90 | 89 | 61 |

What is claimed is:

1. A compound of the formula (I) or a pharmaceutically acceptable salt thereof

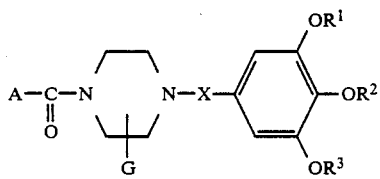

wherein $R^1$, $R^2$ and $R^3$ are lower alkyl groups; A is i) a phenyl group, ii) a hydrocarbon group selected from the class consisting of pentalenyl, indenyl, indanyl, naphthyl, dihydronaphthyl, tetrahydronaphthyl, hexahydronaphthyl, azulenyl, heptalenyl, biphenylenyl, indacenyl, acenaphthylenyl, acenaphthenyl, phenalenyl, phenanthryl, dihydrophenanthryl, tetrahydrophenanthryl, hexahydrophenanthryl, anthryl, dihydroanthryl, tetrahydroanthryl, hexahydroanthryl, octahydroanthryl, fluorenyl, diyhydrofluorenyl, tetrahydrofluorenyl, benzocycloheptenyl, dihydrobenzocycloheptenyl, tetrahydrobenzocycloheptenyl, dibenzocycloheptenyl, naphthocycloheptenyl, dihydronaphthocycloheptenyl, benzocyclooctenyl, dihydrobenzocyclooctenyl, tetrahydrobenzocyclooctenyl, hexahydrobenzocyclooctenyl and octahydrobenzocyclooctenyl, iii) a heterocyclic group selected from the class consisting of pyridyl, thienyl, furyl, thiazolyl, quinolyl, isoquinolyl, indolyl, benzothiazolyl, 1,3-benzodioxolyl, benzofuranyl, 2,3-dihydrobenzofuranyl, benzopyranyl, 3,4-dihydrobenzopyranyl, 1-benzoxepinyl, 2,3-dihydro-1-benzoxepinyl, 2,3,4,5-tetrahydro-1-benzoxepinyl, 1-benzothiepinyl, 2,3-dihydro-1-benzoxepinyl, 2,3,4,5-tetrahydro-1-benzothiepinyl, 3,4-dihydro-2H-1,5-benzoxpinyl, 2,3-dihydro-1,4-benzoxynyl, chromenyl chromanyl, dibenzofuranyl, 3,4-dihydrobenzofuranyl, 1,2,3,4-tetrahydrodibenzofuranyl, dibenzothiophenyl, 3,4-dihydrodibenzothiophenyl, 1,2,3,4-tetrahydrodibenzothiophenyl, naphtho[2,3-d]-1,3-dioxolyl, 5,6-dihydronaphtho[2,3-d]-1,3-dioxolyl, 5,6,7,8-tetrahydronaphtho (8 2,3-d]-1,3-dioxolyl, naphtho[2,3-d]-1,4-dioxanyl, 6,7-dihydronaphtho[2,3-b]-1,4-dioxanyl, 5H-cyclohept[f]-1,3-benzodioxolyl, 6H-cyclohepta [g]-1,4-benzodioxanyl, 7,8-dihydro-6H-cyclohepta [g]-1,4-benzodioxanyl, dibenzo-p-dioxynyl, xanthenyl, 1,2-dihydroxanthenyl, naphtho]2,1-b]furanyl, 1,2,8,9-tetrahydronaphtho[2,1-b]furanyl and 2,3,5,6-tetrahydronaphtho[2,1-b]furanyl, or iv) a styryl group of the formula: $Ar—CR^4=CR^5—$ wherein AR is a phenyl group, and $R^4$ and $R^5$ are independently hydrogen or a lower alkyl group, the phenyl group represented by A or Ar, the hydrocarbon group represented by A, and the heterocyclic group represented by A being unsubstituted or substituted by one or more substituents selected from the class consisting of a lower alkyl group, a halo lower alkyl group, a hydroxy lower alkyl group, a $C_{2-5}$ alkanoyloxy lower alkyl group, a benzoyloxy lower alkyl group, a lower alkoxy lower alkyl group, a lower alkoxy group, a halo lower alkoxy group, a lower alkoxycarbonyl lower alkoxy group, a lower alkenyloxy group, a phenyl-lower alkyloxy group, a lower alkoxy lower alkoxy group, a N,N-di-lower alkylcarbamoyl group, a N-lower alkylcarbamoyl group, halo group, cyano group, nitro group, hydroxy group, $C_{2-5}$ alkanoyloxy group, benzoyloxy group, amino group, a lower alkylsulfonylamino group, $C_{2-5}$ alkanoylamino group, benzamido group, a lower alkoxycarbonylamino group, $C_{2-5}$ alkanoyl group, benzoyl group, mercapto group, a lower alkylthio group, a lower alkylsulfinyl group, a lower alkylsulfonyl group and oxo group; X is methylene group, carbonyl group or thiocarbonyl group and G is a group of the formula: $(—CH_2—)_nZ—R^6$ wherein n is an integer of 0 to 2, Z is O, COO, or $CONR^7$ wherein $R^7$ is hydrogen, or a lower alkyl group, and $R^6$ is hydrogen, or a lower alkyl group.

2. A compound according to claim 1, wherein the phenyl group represented by A or Ar is a phenyl group substituted with 1 to 3 lower alkoxy groups.

3. A compound according to claim 2, wherein the lower alkoxy group is methoxy or ethoxy.

4. A compound according to claim 1, wherein the hydrocarbon group represented by A is a group of the formula:

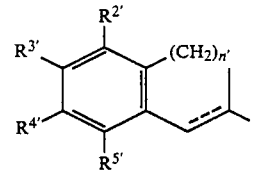

wherein the broken line means possible presence of a double bond; n' is an integer of 1 to 4; and $R^{2'}$, $R^{3'}$, $R^{4'}$, and $R^{5'}$ are independently hydrogen, a lower alkyl group, a halo lower alkyl group, a hydroxy lower alkyl group, a $C_{2-5}$ alkanoyloxy lower alkyl group, a benzoyloxy lower alkyl group, a lower alkoxy lower alkyl group, a lower alkoxy group, a halo lower alkoxy group, a lower alkoxycarbonyl lower alkoxy group, a lower alkenyloxy group, a phenyl-lower alkyloxy group, a lower alkoxy lower alkoxy group, a lower alkoxycarbonyl group, carboxyl group, carbamoyl group, an N,N-di-lower alkylcarbamoyl group, an N-lower alkylcarbamoyl group, halo group, cyano group, nitro group, hydroxyl group, $C_{2-5}$ alkanoyloxy group, benzoyloxy group, amino group, a lower alkylsufonylamino group, $C_{2-5}$ alkanoylamino group, benzamido group, a lower alkoxycarbonylamino group, $C_{2-5}$ alkanoyl group, benzoyl group, mercapto group, a lower alkylthio group, a lower alkylsulfinyl group or a lower alkylsulfonyl group.

5. A compound according to claim 4, wherein $R^{2'}$, $R^{3'}$, $R^{4'}$ and $R^{5'}$ are independently hydrogen, a lower alkoxy group, a phenyl-lower alkyloxy group, a lower alkoxy lower alkoxy group, hydroxyl group, $C_{2-5}$ alkanoyloxy group or benzoyloxy group.

6. A compound according to claim 4, wherein $R^{2'}$ $R^{5'}$ are hydrogen.

7. A compound according to claim 4, wherein n' is 2 or 3.

8. A compound according to claim 4, wherein the broken line means the presence of a double bond.

9. A compound according to claim 1, the hydrocarbon group represented by A is a group of the formula:

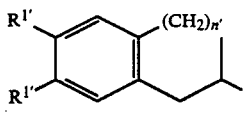

wherein broken line means possible presence of double bond; R¹' is a lower alkoxy group and n' is an integer of 1 to 4.

10. A compound according to claim 9, wherein R¹' is methoxy or ethoxy.

11. A compound according to claim 1, wherein the heterocyclic group represented by A is an oxygen-containing dicyclic or tricyclic heterocyclic group.

12. A compound according to claim 11, wherein the oxygen-containing dicyclic or tricyclic heterocyclic group is a group selected from the class consisting of benzo-1,3-dioxolyl, coumarinyl, 2,3-dihydro-1-benzoxepinyl, dibenzofuranyl, 5,6-dihydronaphtho[2,3-d]-1,3-dioxolyl and 6,7-dihydrocyclohepta[f]-1,3benzodioxolyl.

13. A compound according to claim 1, wherein the heterocyclic group represented by A is a group of the formula:

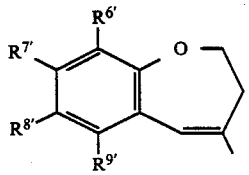

wherein R⁶', R⁷', R⁸' and R⁹' are independently hydrogen, a lower alkyl group, a halo lower alkyl group, a hydroxy lower alkyl group, an $C_{2-5}$ alkanoyloxy lower alkyl group, a benzoyloxy lower alkyl group, a lower alkoxy lower alkyl group, a lower alkoxy group, a halo lower alkoxy group, a lower alkoxycarbonyl lower alkoxy group, a lower alkenyloxy group, a phenyl-lower alkyloxy group, a lower alkoxy lower alkoxy group, a lower alkoxycarbonyl group, carboxyl group, carbamoyl group, an N,N-di-lower alkylcarbamoyl group, an N-lower alkylcarbamoyl group, halo group, cyano group, nitro group, hydroxyl group, $C_{2-5}$ alkanoyloxy group, benzoyloxy group, amino group, a lower alkylsulfonylamino group, $C_{2-5}$ alkanoylamino group, benzamido group, a lower alkoxycarbonylamino group, $C_{2-5}$ alkanoyl group, benzoyl group, mercapto group, a lower alkylthio group, a lower alkylsulfinyl group or a lower alkylsulfonyl group.

14. A compound according to claim 13, wherein R⁶', R⁷', R⁸' and R⁹' are independently hydrogen, a lower alkyl group or a lower alkoxy group.

15. A compound according to claim 14, wherein R⁶' and R⁹' are hydrogen.

16. A compound according to claim 15, wherein R⁶' and R⁸' are a lower alkoxy group.

17. A compound according to claim 16, wherein the lower alkoxy group is methoxy or ethoxy.

18. A compound according to claim 1, wherein R¹, R² and R³ are methyl.

19. A compound according to claim 1, wherein X is methylene group or carbonyl group.

20. A compound according to claim 1, wherein Z is O, COO or CONR⁷ wherein R⁷ is hydrogen or a lower alkyl.

21. A compound according to claim 20, wherein the lower alkyl is methyl or ethyl.

22. A compound according to claim 1, wherein R⁶ is hydrogen or a lower alkyl.

23. A compound according to claim 22, wherein the lower alkyl is methyl or ethyl.

24. A compound according to claim 1, wherein X is methylene group or carbonyl group; A is a phenyl group substituted with 2 to 3 lower alkoxy groups, a group of the formula:

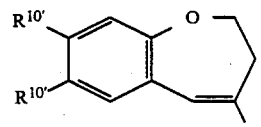

wherein R¹⁰' is a lower alkoxy group or a group of the formula:

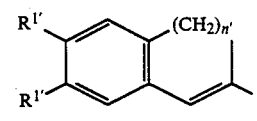

wherein R¹' is a lower alkyl group and n' is an integer of 2 or 3.

25. A compound according to claim 1, which is 1-(2,3-dimethoxy-6,7-dihydro-5H-benzocyclohepten-8-ylcarbonyl) -3-methoxymethyl-4-(3,4,5-trimethoxybenzoyl)piperazine.

26. A compound according to claim 1, which is 1-(2,3-dimethoxy-6,7-dihydro-5H-benzocyclohepten-8-ylcarbonyl) -3-methoxymethyl-4-(3,4,5-trimethoxybenzyl)piperazine.

27. A compound according to claim 1, which is 1-[2(3,4-dimethoxyphenyl) thiazol-4-ylcarbonyl]-2-methoxymethyl-4-(3,4,5-trimethoxybenzoyl) piperazine.

28. A compound according to claim 1, which is 1-[2-(3,4-dimethoxyphenyl) thiazol-4-ylcarbonyl]-2-methoxymethyl-4-(3,4,5-trimethoxybenzyl) piperazine.

29. A compound according to claim 1, which is 1-[2-(3,4-difluorophenyl) thiazol-4-ylcarbonyl]-2-methoxymethyl-4-(3,4,5-trimethoxybenzyl) piperazine.

30. A pharmaceutical composition suitable for inhibiting activities of platelet activating factor which comprises
  (a) as the active ingredient, an amount effective to inhibit activities of platelet activating factor of a compound as claimed in claim 1 or a pharmaceutically acceptable salt thereof and
  (b) a pharmaceutically acceptable carrier or excipient therefor.

31. A method for inhibiting activities of platelet activating factor in a mammal, which comprises administering to said mammal an amount effective to inhibit activities of platelet activating factor of a compound as claimed in claim 1 or a pharmaceutically acceptable salt thereof, or a pharmaceutical composition as claimed in claim 30.

32. A compound according to claim 1, wherein G is a group of the formula —CH₂—O—(lower alkyl).

* * * * *